US009474724B2

(12) United States Patent
Gierhart

(10) Patent No.: US 9,474,724 B2
(45) Date of Patent: *Oct. 25, 2016

(54) ZEAXANTHIN FORMULATIONS WITH ADDITIONAL OCULAR-ACTIVE NUTRIENTS, FOR PROTECTING EYE HEALTH AND TREATING EYE DISORDERS

(71) Applicant: ZeaVision LLC, Chesterfield, MO (US)

(72) Inventor: Dennis L. Gierhart, Chesterfield, MO (US)

(73) Assignee: ZeaVision LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/861,803

(22) Filed: Sep. 22, 2015

(65) Prior Publication Data
US 2016/0008296 A1 Jan. 14, 2016

Related U.S. Application Data

(63) Continuation of application No. 10/746,403, filed on Dec. 23, 2003, now Pat. No. 9,192,586.

(60) Provisional application No. 60/453,522, filed on Mar. 10, 2003.

(51) Int. Cl.
| | | |
|---|---|---|
| *A61K 31/07* | (2006.01) | |
| *A61K 31/12* | (2006.01) | |
| *A61K 31/047* | (2006.01) | |
| *A61K 9/00* | (2006.01) | |

(52) U.S. Cl.
CPC ........... *A61K 31/047* (2013.01); *A61K 9/0048* (2013.01); *A61K 31/07* (2013.01)

(58) Field of Classification Search
CPC ............................ A61K 31/07; A61K 31/047
See application file for complete search history.

(56) References Cited

U.S. PATENT DOCUMENTS

| | | |
|---|---|---|
| 3,841,967 A | 10/1974 | Dasek |
| 3,879,424 A | 4/1975 | Surmatis |
| 3,891,504 A | 6/1975 | Schocher |
| 3,920,834 A | 11/1975 | Klaui |
| 3,932,462 A | 1/1976 | Goetz |
| 3,951,743 A | 4/1976 | Shepherd |
| 3,954,804 A | 5/1976 | Fischer |
| 3,974,181 A | 8/1976 | Surmatis |
| 4,078,094 A | 3/1978 | Katzen |
| 4,153,615 A | 5/1979 | Saucy |
| 4,298,621 A | 11/1981 | Samis |
| 4,405,417 A | 9/1983 | Grass |
| 4,522,743 A | 6/1985 | Horn |
| 4,579,973 A | 4/1986 | Widmer |
| 4,726,955 A | 2/1988 | Horn |
| 4,851,339 A | 7/1989 | Hills |
| 4,935,409 A | 6/1990 | Wollweber |
| 4,952,716 A | 8/1990 | Lukac |
| 5,075,116 A | 12/1991 | LaHaye |
| 5,180,747 A | 1/1993 | Matsuda |
| 5,227,507 A | 7/1993 | Lukac |
| 5,242,950 A | 9/1993 | Fries Hastings |
| 5,290,605 A | 3/1994 | Shapira |
| 5,308,759 A | 5/1994 | Gierhart |
| 5,310,764 A | 5/1994 | Baranowitz |
| 5,350,773 A | 9/1994 | Schweikert |
| 5,356,636 A | 10/1994 | Schneider |
| 5,360,730 A | 11/1994 | Orndorff |
| 5,382,714 A | 1/1995 | Khachik |
| 5,386,063 A | 1/1995 | Khachik |
| 5,427,783 A | 6/1995 | Gierhart |
| 5,429,939 A | 7/1995 | Misawa |
| 5,437,997 A | 8/1995 | Liao |
| 5,523,494 A | 6/1996 | Torres-Cardona |
| 5,527,533 A | 6/1996 | Tso |
| 5,607,707 A | 3/1997 | Ford |
| 5,607,839 A | 3/1997 | Tsubokura |
| 5,684,238 A | 11/1997 | Ausich |
| 5,739,156 A | 4/1998 | Bissett |
| 5,770,217 A | 6/1998 | Kutilek |
| 5,777,173 A | 7/1998 | Paust |

(Continued)

FOREIGN PATENT DOCUMENTS

| | | |
|---|---|---|
| EP | 0 747 483 A2 | 12/1996 |
| WO | WO 96/40092 A1 | 12/1996 |

(Continued)

OTHER PUBLICATIONS

Bendich, A., et al, "Biological actions of carotenoids," FASEB Journal 3: 1927-1932 (1989).
Bone, R.A., et al, "Preliminary identification of the human macular pigment," Vision Res. 25: 1531-1535 (1985).
Bone R.A., et al, "Stereochemistry of the macular carotenoids," Invest. Ophthalmol. Vis. Sci. 34: 2033-2040 (1993).
Columbo, V.E., et al, "Structures and properties of stabilized vitamin and carotenoid dry powders," Food Structure 10: 161-170 (1991).
Di Mascio, P., et al, "Lycopene as the most efficient biological carotenoid singlet oxygen quencher," Archives of Biochemistry and Biophysics 274: 532-538 (1989).
Di Mascio, P., et al, "Antioxidant defense systems: the role of carotenoids, tocopherols, and thiols," Am. J. Clin. Nutr. 53: 194S-200S (1991).

(Continued)

*Primary Examiner* — Zohreh Fay
(74) *Attorney, Agent, or Firm* — Nixon Peabody LLP

(57) ABSTRACT

Oral formulations for promoting eye health, and in particular for preventing or treating macular degeneration, are disclosed, containing zeaxanthin, a carotenoid pigment, and at least two or more additional ocular-active nutrients selected from lipoic acid, omega-3 fatty acids, plant-derived compounds such as flavonoids, anthocyanins, or polyphenolics, taurine, carnitine, Coenzyme-Q10, carnosine, and nutrients that stimulate the production of glutathione. Processes are disclosed for identifying ocular-active nutrients that will interact in a synergistic and potentiating manner with zeaxanthin, to provide better and more effective protection, for eye health, than can be provided by zeaxanthin alone. Additional optional agents include zinc, vitamin E, and vitamin C.

14 Claims, 2 Drawing Sheets

(56) References Cited

U.S. PATENT DOCUMENTS

| | | | |
|---|---|---|---|
| 5,780,693 | A | 7/1998 | Bernhard |
| 5,871,766 | A | 2/1999 | Hennekens |
| 5,948,443 | A | 9/1999 | Riley |
| 5,976,568 | A | 11/1999 | Riley |
| 6,020,351 | A | 2/2000 | Pero |
| 6,103,756 | A | 8/2000 | Gorsek |
| 6,218,436 | B1 | 4/2001 | Howard |
| 6,573,299 | B1 | 6/2003 | Petrus |
| 6,649,195 | B1 | 11/2003 | Gorsek |
| 6,660,297 | B2 | 12/2003 | Bartels |
| 2001/0009926 | A1 | 7/2001 | Howard |
| 2001/0031744 | A1 | 10/2001 | Kosbab |

FOREIGN PATENT DOCUMENTS

| | | |
|---|---|---|
| WO | WO 02/47493 | 6/2002 |
| WO | WO 2005/063223 | 7/2005 |

OTHER PUBLICATIONS

Dorey, C.K., et al, "Lipofuscin in aged and AMD eyes," in Retinal Degeneration (Hollyfield et al., editors, Plenum Press, New York, 1993).

Eye Disease Case Control Study Group, "Antioxidant status and neovascular age-related macular degeneration," Arch. Ophthalmol. 11: 104-109 (1993).

Gerster, H., "Review: antioxidant protection of the aging macula," Age and Aging 20: 60-69 (1991).

Haegerstrom-Portnoy, G., "Short-wavelength-sensitive-cone sensitivity loss with aging: a protective role for macular pigment?," J. Opt. Soc. Am. A5: 2140-2144 (1988).

Handelman, G.J. and Dratz, E.A., "The role of antioxidants in the retina and retinal pigment epithelium and the nature of prooxidant-induced damage," Adv. in Free Radical Biology & Medicine 2: 1-23 and 55-57 (1986).

Handelman, G.J., et al, "Carotenoids in the human macula and whole retina," Invest. Ophthalmol. Vis. Sci. 29: 850-855 (1988).

Malinow, M.R., et al, "Diet-related macular anomalies in monkeys," Invest. Ophthalmol. Vis. Sci. 19: 857-863 (1980).

National Advisory Eye Council, Vision Research: A National Plan, 1994-1998 (NIH Publication 93-3186), pp. 55-64, 336, and 356(1998).

Seddon, J.M., et al, "Dietary carotenoids, vitamins A, C, and E, and advanced age-related macular degeneration," JAMA 272: 1413-1420 (1994).

Sperduto, R.D., et al, "Do we have a nutritional treatment for age-related cataract or macular degeneration?," Arch. Ophthalmol. 108: 1403-1405 (1990).

Supplementary European Search Report for European Application No. 04 81 5753 dated Mar. 4, 2009 (3 pages).

Taylor, A., et al, "Oxidation and aging: impact on vision," Journal of Toxicology and Industrial Health 9:349-371 (1993).

"Flora-Glo Lutein" product specification sheets (Kemin Industries Inc., Des Moines, Iowa, 1997).

Alpers, J.R., et al, "Serum Carotenoids and Age-Related Macular Degeneration," Invest Ophthalmol Vis Sci 36: S9 (1995).

Ascherio, A., et al, "Correlations of Vitamin A and E Intakes with the Plasma Concentrations of Carotenoids and Tocopherols among American Men and Women," J of Nutrition 122 (9): 1792-1801 (1992).

Bertram, J.S., et al, "Diverse carotenoids protect against chemically induced neoplastic transformation," Carcinogenesis 12 (4): 671-678 (1991).

Blumenkranz, M.S., et al, "Risk factors in age-related maculopathy complicated by choroidal neovascularization," Ophthalmology 93: 552-558 (1986).

Bone, R.A., et al, "Distribution of macular pigment stereomers in individual eyes, including those with age-related macular degeneration (AMD)," Arvo Abstracts Invest Ophthalmol Vis Sci V.35: 4 pp. 1502 (1994).

Bone, R.A., et al, "Analysis of the macular pigment by HPLC: retinal distribution and age study," Invest Ophthalmol Vis Sci 29: 843-9 (1988).

Bone, R.A., "The role of the macular pigment in the detection of polarized light," Vision Research 30: 213-220 (1979).

Bowmaker, J.D., et al, "Visual pigments and oil droplets in genetically manipulated and carotenoid deprived quail: a microspectrophotometric study," Vision Res 33: 571-578 (1993).

Burton, G.W., "Antioxidant action of carotenoids," American Institute of Nutrition, 109-111 (1988).

Castorina, C., et al, "Lipid peroxidation and antioxidant enzymatic systems in rat retina as a function of age," Neurochem Res 17(6): 599-604 (1992).

Christen, W.G., "Antioxidants and eye disease," The Amer J of Medicine 97 (suppl 3A): 3A-142-3A-162 (1994).

Conn, P.F., et al, "The singlet oxygen and carotenoid interaction," J Photochem Photobiol B Biol 11: 41-47 (1991).

Crary, E.J., "Antioxidant treatment of macular degeneration of the aging and macular edema in diabetic retinopathy," Southern Med J 80: 38 (1997).

Fite, K.V., "Drusen-like deposits in the outer retina of Japanese quail," Exp Eye Res 59: 417-424 (1994).

Fite, K.V., et al, "Experimental light damage increases lipofuscin in the retinal pigment epithelium of Japanese quail," Exp Eye Res 57: 449-460 (1993).

Fite, K.V., et al, "Age, sex and light damage in the avian retina: a model system," P. Bagnoli et al, Ed, The Changing Visual System: 283-294 (1991).

Foote, C.S., et al, "Chemistry of singlet oxygen. X. Carotenoid quenching parallels biological protection," J Amer Chem Soc 92: 17 (1970).

Goldberg, J., et al, "Factors Associated with Age-Related Macular Degeneration: An analysis of Data from the First National Health and Nutrition Examination Survey," Am J Epidemiol 128(4): 700-10 (1988).

Gottsch, J.D., et al, "Hematogenous photosensitization," Inves Opthamol & Vis Sci 31(9): 1674-1682 (1990).

Gruszecki, W.I., et al, "Orientation of xanthophylls in phosphatidylcholine multibilayers," Biochim Biophys Acta 1023(3): 405-412 (1990).

Ham, W.T., et al, "Basic mechanisms underlying the production of photochemical lesions in the mammalian retina," Curr Eye Res 3(1): 165-174 (1984).

Ham, W.T., et al, "The photopathology and nature of the blue-light and near-UV retinal lesions produced by lasers and other optical sources," ed. Plenum Press; New York, Laser Application in Medicine and Biology: 191-246 (1989).

Hockwin, O., et al, "Investigations on lens transparency and its disturbances by microdensitometric analyses of Scheimpflug photographs," Curr Eye Res 3(1): 15-22 (1984).

Hope, G.M., et al, "A primate model for age related macular drusen," British J of Ophthalmol 76: 11-16 (1992).

Kahn, H.A., et al, "Framingham Eye Study 1. Outline and major prevalence finding," Am J Epidemiol 106(1): 17-32 (1977).

Khachik, F., et al, "Lutein, lycopene, and their oxidative metabolites in chemoprevention of cancer," J of Cell Biochem S22: 236-246 (1995).

Khachik F., et al, "Separation and identification of carotenoids and their oxidation products in the extracts of human plasma," Anal Chem 64: 2111-22 (1992).

Kirschfeld, K., "Carotenoid pigments: their possible role in protecting against photooxidation in eyes and photoreceptor sells," Proc R Soc London B 216: 71-85 (1982).

Klaui, H. and Bauerenfeind, C.J., pp. 86-102 in Carotenoids as colorants and vitamin A precursors, Baurenfeind, C.J., Ed, Academic Press (1981).

Klein, R., et al, "Racial/ethnic differences in age-related maculopathy. Third National Health and Nutrition Examination Survey," Opthamology 102(3): 371-81 (1995).

Klein, B., et al, "Prevalence of Age-related Lens Opacities in a Population: The Beaver Dam Eye Study," Ophthalmol 99(4): 546-52 (1992).

(56) References Cited

OTHER PUBLICATIONS

Mangels, A.R., et al, "Carotenoid content of fruits and vegetables: an evaluation of analytical data," J Amer Diet Assn 93(3): 284-96 (1993).

Mares-Perlman, J.A., et al, "Serum antioxidants and age-related macular degeneration in a population-based case-control study," Arch Ophthalmol 113: 1518-1523 (1995).

Monaco, W.A., et al, "The rhesus monkey as an animal model for age-related maculopathy," Optometry Vis Sci 67(7): 532-537 (1990).

Nussbaum, J.J., et al, "Historic perspectives Macular yellow pigment. The first 200 years," Ophthal Comm Soc 1(4): 296-310 (1981).

Parker, R.S., "Carotenoids in human blood and tissues," Amer Inst Nutr: 101-104 (1988).

Pease, P.L., et al, "Optical density of human macular pigment," Vis Res 27(5): 705-710.

Sanders, T.A.B., et al, "Essential fatty acids, plasma cholesterol, and fat-soluble vitamins in subjects with age-related maculopathy and matched control subjects," Am J Clin Nutr 57: 428-433 (1993).

Schalch, W., "Carotenoids in the retina—a review of their possible role in preventing or limiting damage caused by light and oxygen," Emerit I., et al, Ed, Free Radicals and Aging: 280-298 (1992).

Seddon, J.M., et al, "Vitamins, minerals, and macular degeneration: Promising but unproven hypotheses," Arch Ophthalmol 112: 176-179 (1994).

Snodderly, D.M., "Evidence for protection against age-related macular degeneration by carotenoids and antioxidant vitamins," Am J Clin Nutr 62(Suppl): 1448S-61S (1995).

Snodderly, D.M., et al, "The macular pigment. I. Absorbance spectra, localization, and discrimination from other yellow pigments in primate retinas," Invest Ophthalmol Vis Sci 25: 660-673 (1984a).

Snodderly, D.M., et al, "The macular pigment. II. Spatial distribution in primate retinas," Invest Ophthalmol Vis Sci 25: 674-85 (1984b).

Snodderly, D.M., et al, "Distribution of individual macular pigment carotenoids in central retina of macaque and squirrel monkeys," Invest Ophthalmol Vis Sci 32(2): 268-279 (1991).

Stone, W.L., et al, "A reinvestigation of the fatty acid content of bovine, rat and frog retinal rod outer segments," Exp Eye Res 28: 387-397 (1979).

Sunness, J.S., et al, "Diminished foveal sensitivity may predict the development of advanced age-related macular degeneration," Ophthalmol 96(3): 375-381 (1989).

Taylor, H.R., et al, "The long-term effects of visible light on the eye," Arch Ophthalmol 110: 99-104 (1992).

Thylefors, B., et al, "Global Data on Blindness," Bulletin of the World Health Organization 73(1): 115-121 (1995).

Vingerling, J.R., "Epidemiology of age-related maculopathy," Epidemiol Rev 17(2): 347-360 (1995).

Weiser, J., et al, "Provitamin A activities and physiological functions of carotenoids in animals: relevance to human health," Ann NY Acad Sci 691: 213-215 (1993).

Weiter, J.J., et al, "Central sparing in annular macular degeneration," Am J Ophthalmol 106: 286-292 (1988).

Werner, J.S., "Aging and human macular pigment density," Vis Res 27(2): 257-268 (1987).

West, S., et al, "Epidemiology of risk factors for age-related cataracts," Survey Ophthalmol 39(4): 323-34 (1995).

West, S., et al, "Are antioxidants or supplements protective for age-related macular degeneration?," Arch Ophthalmol 112: 222-227 (1994).

National Eye Advisory Council, pp. 13-38 in Vision Research—A National Plan: 1999-2003 (NIH Publ. 99-4120, 1999).

Jampol, L.M., "Antioxidants, zinc, and age-related macular degeneration," Arch Ophthalmol 119: 1533-1534 (2001).

AREDS Research Group, Report No. 8, "A randomized, placebo-controlled, clinical trial of high-dose supplementation with vitamins C and E, beta carotene, and zinc for age-related macular degeneration and vision loss," Arch Ophthalmol 119: 1417-1436 (2001).

Widmer et al, "Technical Procedures for the Synthesis of Carotenoids and Related Compounds from 6-Oxo-Isophrone: Synthesis of (3R-3'R) Zeaxnathin" Helvetica Chemica Acta, 73, 861-867 (1990).

"Do Antioxidants prevent or Retard the Onset of AMD?", J. Amer. Osteopathic Assn. 95(1): 26 (Jan. 1995).

"The Effect of a Dietary Lack of Xanthophyll on the Eye of the Monkey," Nutrition Reviews 38: 384-386 (1980).

Landrum, J.T., et al, " Macular Pigment Stereomers in Individual Eyes: A Comparison Between Normals and Those With Age-Related Macular Degeneration" (abstract), Invest. Opthalm. Visual Sci. 36(4): S895 (Conference Proceedings, Mar. 15, 1995).

Hammond, B.R., "The Relationship Between Cigarette Smoking and Peak Macular Pigment Density," Invest. Opthalm. Visual Sci. 36(4): S233 (Conference Proceedings, Mar. 15, 1995).

International Search Report, PCT/US2004/043743, 2 pages, date of mailing May 10, 2005.

International Written Opinion, PCT/US2004/043743, 3 pages, date of mailing May 10, 2005.

Watery fluid outside cell

Oily interior of cell membrane

Watery fluid inside cell

ZEAXANTHIN FORMULATIONS WITH ADDITIONAL OCULAR-ACTIVE NUTRIENTS, FOR PROTECTING EYE HEALTH AND TREATING EYE DISORDERS

RELATED APPLICATION

This application is a continuation of U.S. application Ser. No. 10/746,403, filed Dec. 23, 2003, now allowed, which claims the benefit of priority of U.S. Provisional Patent Application No. 60/453,522, filed Mar. 10, 2003, each of which are incorporated by reference in their entirety.

FIELD OF THE INVENTION

This invention is in the fields of biochemistry, pharmacology, and nutritional supplements, and relates to orally-ingested formulations for treating or preventing eye diseases and vision problems.

BACKGROUND OF THE INVENTION

Hundreds of different dietary supplements, under thousands of different brand and product names, are being marketed to the public in the U.S. and elsewhere, by means of advertising promises and claims which suggest that these products can help prevent or treat eye diseases, and maintain eye health. Faced with an overwhelming glut of competing promises and products, nearly all of which are unproven and many of which have only tenuous and flimsy support, it has become effectively impossible for people who are concerned about eye health to know which products will help, and which are merely preying on innocent victims whose vision is deteriorating, either because of general aging problems, or due to specific diseases, infections or injuries.

Indeed, severe uncertainties and doubts about which dietary supplements are effective extend to full-time professionals who specialize in eye research, or in treating eye diseases. Many examples to support this assertion can be cited, including numerous current and recent articles, in respected scientific and medical journals, stating that not enough evidence is available to allow physicians to know whether to recommend various candidate dietary supplements to their patients.

Along those same lines, the recent AREDS (Age-Related Eye Disease Study) study, which was organized and carried out by the National Eye Institute at a cost of tens of millions of dollars, tested vitamins C and E (as well as beta-carotene) at high dosages. They offered a low and weak level of protection against macular degeneration, in some but not all of the patient categories, in the AREDS-1 trial. Similarly, zinc at very high dosages (80 mg/day), by itself, offered a low and weak level of protection in some categories of patients. When vitamins A/C/E and zinc were combined, the level of protection increased, especially among late-stage macular degeneration sufferers. Accordingly, the results and findings of the AREDS-1 trial are not regarded as strong or compelling, when compared with the potential benefits of zeaxanthin, and in recent years it also has become clear that high dosages of vitamin A or its precursor, beta carotene, offer little or no serious hope for providing any significant protection against macular degeneration, or any other serious eye disorders among people who receive minimal baseline levels of vitamin A.

As a direct response to the positive claims of the AREDS managers, one skilled observer (Siegel 2002) publicly and openly complained that the purported benefits could be teased out of the data only by massaging the data in ways that, instead of being objective, impartial, and scientific, were instead biased and intended to locate something positive to report, to offset the fact that the entire remainder of the study had spent many millions of dollars but had come up empty. In the words of that expert, "In my opinion the AREDS investigators promoted a nonsignificant result into a conclusive recommendation. Here is how they did it . . . the message that should have emerged from AREDS is that these treatments failed to demonstrate efficacy in preventing AMD and are not recommended for that use." Even reviewers who endorsed the AREDS findings had to include various cautions and caveats; as one example, in an editorial that accompanied the AREDS report, in the same issue of the same journal, the reviewer had to include statements such as, "The exclusion of the subgroup of patients in Category 2 from many of the analyses because of the low incidence of primary outcome events in troubling because it came after review of the data."

Other experts in eye research, and ophthalmologists who specialize in treating patients with serious eye problems, do not and cannot agree on the roles of either or both of two carotenoid pigments that are known to exist naturally in the retina. Those two pigments are called lutein and zeaxanthin. However, even though nearly 20 years have passed since Bone at al 1985 identified those two carotenoid pigments as the agents that give the "macula" (a small yellowish spot in the center of the retina, which is crucial for clear vision) its yellowish color, experts in eye research and eye diseases cannot and do not agree on what roles those two carotenoids play in the retina, or whether either or both of them should be recommended as dietary supplements. Evidence to support and prove this conclusion is available from numerous sources, both published and unpublished. As one example of a published report, a large panel of highly respected experts who specialize in retinal diseases was brought together in 1998 by the National Eye Institute (NEI), and the experts were asked to develop strategic proposals and recommendations that would guide the NEI's funding for eye research over the next five years. That panel reviewed a wide range of options and candidate treatments, and specifically identified and named about 60 candidate treatments that the experts thought were deserving of careful scientific study and research grants. Even though that panel of experts identified nearly 60 specific research leads, it never even mentioned lutein or zeaxanthin. That omission could not have been a mere oversight due to a lack of available information, since a number of members of that panel had previously written and published papers that had explicitly discussed lutein and zeaxanthin.

Numerous other researchers who specialize in eye and vision studies also have stated that no reliable conclusions can yet be reached on whether lutein and/or zeaxanthin can actually benefit the eyes to a point where they should be recommended as nutritional supplements. Examples of such recently-published conclusions include Schalch 2000, and Jampol 2001. Schalch 2000 states, at page 38, "Epidemiological studies therefore cannot provide definite proof of the efficacy of lutein and zeaxanthin in AMD. Such studies can provide evidence of possible relationships but cannot determine whether an effect is causal. The situation is different with intervention studies in which agents are administered on a double-masked, placebo-controlled, randomized basis and results are evaluated using predefined efficacy parameters. In the case of supplementation with lutein and zeaxanthin, where only small to moderate responses can be expected, only studies such as these are likely to provide a definite answer as to an effect of lutein and zeaxanthin on AMD. However, the specific time-course and nature of this disease makes the design of such trials difficult." Jampol 2001, at page 1534, states, "In view of previous studies suggesting that beta-carotene might be harmful in smokers and may be associated with a greater risk of lung cancer, beta carotene should probably not be used by smokers and recent ex-smokers. An argument could be made that another carotenoid, lutein or zeaxanthin, could be substituted for beta carotene, but the values and risks of other carotenoids [apparently referring gain to lutein and zeaxanthin] is unknown at this time."

As another example of the uncertainties and doubts that surround zeaxanthin among skilled physicians who treat eye diseases, the Inventor has personal knowledge of a patient who has the "wet" (or "exudative") form of macular degeneration. This disease is characterized by aggressive growth of capillaries in and around certain layers of the retina, and it leads to rapid and devastating loss of vision. The best known treatment for wet AMD is called laser photocoagulation, or photodynamic therapy. It uses a drug called verteporfin, which is activated by a laser that is shone directly into the eyes of patients who have taken the drug. In October of 2003, a ZeaVision customer (a male in his late 70's) who was taking zeaxanthin capsules on a daily basis was scheduled to have a laser treatment using verteporfin, at the Wilmer Eye Institute in Baltimore, which is affiliated with the Johns Hopkins School of Medicine. This patient told his treating physician, who is one of the top experts in the world on treating macular degeneration, that he was taking zeaxanthin capsules on a daily basis. The treating physician suggested that the patient should stop taking zeaxanthin, since it probably would not help. Despite that suggestion, the patient continued taking zeaxanthin, up through the date of the treatment and continuing thereafter. The results of that treatment, as measured up until the date this is being written, have been outstanding, and have been much better than was expected by the treating physician. That discovery is the subject of a recently-filed provisional patent application that will be disclosed to the companies that manufacture and sell verteporfin, and to a number of physicians who perform laser-verteporfin treatments, so they can evaluate it in a clinical trial using numerous patients. For now, the point worth noting is this: when advised that a patient suffering from wet macular degeneration was taking zeaxanthin, one of the top eye experts in the world advised the patient that he should stop taking it.

This current invention centers on zeaxanthin, which is believed by the Inventor to be an essential and crucial ingredient in any optimal or near-optimal pharmaceutical formulations and/or dietary supplements that will be truly effective in protecting, treating, and otherwise improving various aspects of eye health. A number of reasons for believing and asserting that zeaxanthin is and will be the essential and crucial ingredient in such formulations (including factors indicating that zeaxanthin will perform substantially better than lutein, in this role) are set forth below, to justify these assertions and beliefs by the Inventor despite lingering refusals by other skilled researchers and eye care companies to recognize zeaxanthin's role as a crucial and essential agent for protecting and preserving eye health.

It might be asserted that each factor summarized in the next section is already known and published, in the prior art. However, it must also be recognized that (i) these factors have never previously been combined and correlated, in the manner set forth herein; and, (ii) the non-obviousness of the invention disclosed herein must also be evaluated in light of evidence which clearly shows that numerous highly-skilled experts do not believe zeaxanthin has any proven role in protecting or restoring eye health.

INFORMATION ON ZEAXANTHIN IN EYE HEALTH

The use of zeaxanthin for treating and preventing macular degeneration is described in several US patents, including U.S. Pat. No. 5,747,544 (Garnett et al 1997) on methods of use, and reissue Pat. Re-38,009 (Garnett et al 2003, which replaced U.S. Pat. No. 5,827,652, Garnett et al 1998) on formulations for human ingestion. The contents and teachings of those patents are incorporated herein by reference, as though fully set forth herein.

Additional review articles that discuss the roles and the assumed, purported, or likely effects of zeaxanthin and lutein, in mammalian eyes, is provided in a number of articles, including Snodderly 1995, Landrum et al 1997, Schalch et al 1999, Schalch 2000, and Semba et al 2003.

Zeaxanthin and lutein both belong to a class of molecules called carotenoids, which are created by plants. "Carotenoids" were given that name, because they were first isolated from carrots.

Carotenoids have two traits that make them very important in nature and nutrition: (1) they're very good at absorbing ultraviolet (UV) and blue light; and (2) just like vitamins, they cannot be synthesized inside the cells or bodies of humans, or other mammals. Therefore, humans and other mammals must eat carotenoids in food, or in dietary supplements, to get the amounts they need.

Since the UV radiation in direct sunlight, shining directly on cells for numerous hours each day, is strong enough to kill any type of unprotected cell, carotenoids play crucially important role in plants, and in many types of bacteria. Hundreds of slightly different types of carotenoids have evolved in different species of plants and bacteria; over 600 distinct types of carotenoids have been identified in nature, and every year another dozen or more mare announced. All of those carotenoids are synthesized only in plants or bacteria. Animals (including humans) simply cannot make carotenoids; instead, we must eat the carotenoids we need, in our diets.

An important fact of physics is that light rays with very short wavelengths, in the ultraviolet ("UV"), near-ultraviolet, and deep blue parts of the spectrum, contain the most energy of any wavelengths in or near the visible spectrum. UV and near-UV rays are what turn sunburned skin a painful shade of red. Sunburn is a defense mechanism; when the outer layers of skin become damaged, they respond by swelling up, becoming engorged with blood, histamine, and other agents, and generating and recruiting higher levels of pigment in an effort to reduce the amount of additional damage. UV rays will kill the outermost layers of cells of the skin; when unburned skin begins to peel, those are dead skin cells, coming off.

In the same way, UV rays are a very effective way to sterilize surfaces, because they will kill nearly any types of viruses or bacteria they can reach and hit.

UV rays inflict this type of damage by breaking apart biomolecules more or less randomly. When a ray or photon of UV radiation hits various types of chemical bonds that hold together adjacent atoms in biomolecules, it typically breaks the bond between those two atoms, thereby splitting the molecule into two fragments.

By splitting apart biomolecules on a random basis, UV radiation inflicts two different types of toxic and potentially lethal damage on cells. First, UV radiation will directly break apart the long molecular strands that make up protein and DNA. Since protein and DNA are crucial to any cell, this type of damage will directly kill cells, if it continues long enough. The second mechanism is this: when UV radiation hits a molecule that contains oxygen, it often causes an oxygen-containing fragment to be broken off of the molecule, in a way that creates a highly unstable and reactive "oxygen free radical". Because of complicated factors involving the electrons in an oxygen atom's "valence shell", these unstable free radicals will attack, alter, and damage nearly any type of biomolecule.

To minimize that type of damage from oxygen free radicals, cells use various types of anti-oxidants, which are molecules that will attract and react with oxygen free radicals. A good anti-oxidant molecule will bind any oxygen free radicals into larger molecules, which are stable and will not attack other molecules. This type of neutralizing reaction, by anti-oxidant molecules which absorb and neutralize oxygen free radicals, is often referred to as "quenching," in a manner similar to quenching a fire.

Carotenoids are very effective anti-oxidants, and they can quench and neutralize oxygen free radicals. Therefore, plants evolved with carotenoids as a special class of protective molecules, which can minimize damage that otherwise would be cause by ultraviolet radiation. The surface cells that cover plant leaves contain large quantities of carotenoids. Indeed, carotenoids are what causes tree leaves to turn red, orange, and gold in the fall. Since carotenoids absorb light with blue and violet wavelengths, the wavelengths that bounce off and are reflected and emitted, by the leaves, are at the other end of the color spectrum, in the red, orange, and yellow region. When cold weather arrives and tree leaves become inactive, any green chlorophyll which remains in the leaves is degraded more rapidly than carotenoids, which are rather stable molecules. This causes the red, yellow and orange carotenoids to become the dominant colors in leaves, during the fall.

Bacteria growing in places exposed to direct sunlight for hours require the same type of protection against toxic UV rays. This is why scum that grows on rocks in a river (if it is not made of green algae with chlorophyll) is usually some shade of yellow, brown, or orange. Bacteria that can survive in such locations have evolved the ability to synthesize carotenoids, to protect the bacteria from being killed by UV radiation.

Carotenoids can absorb UV radiation and neutralize oxygen free radicals, without being broken apart, because they contain numerous "conjugated bonds". This is a complicated term, but it can be explained by pointing out an important fact in FIG. 1, which is a drawing of the chemical structures of zeaxanthin and lutein (with beta-carotene also shown, for comparative purposes).

In the straight chain portion (i.e., the chain that stretches between the two "end rings") of all three carotenoids shown in FIG. 1, the double bonds alternate with single bonds. This pattern of alternating single-bonds and double-bonds is referred to by chemists as "conjugation". It is important, because when a series of single and double bonds, all in a row or circle, are conjugated, the electrons that form the bonds between adjacent atoms do not remain attached to specific atoms. Instead, the electrons become mobile, and they form an "electron cloud" that covers and surrounds the molecule. This same type of semi-mobile electron cloud also surrounds and stabilizes benzene rings and other "aromatic" organic molecules.

This type of semi-mobile electron cloud is important, because it leads to a remarkable result. When a carotenoid molecule is hit by a UV ray or an oxygen free radical, the molecule doesn't break. Instead, the electron cloud is able to flex and yield, in a way that cushions and absorbs the blow. This is comparable to someone hitting a wooden board, or a rubber tire, with a sledgehammer. The board will break, because it cannot bend or deflect. The rubber tire will not break, because it can flex and yield in a way that allows it to absorb the force of the blow.

Because their semi-mobile electron clouds are flexible and yielding rather than rigid, carotenoid molecules can absorb numerous "hits" from UV rays and oxygen free radicals, without being broken part. When a UV photon or an oxygen free radical hits a carotenoid, the destructive power of that photon or free radical is used up and absorbed by the electron cloud. The photon or free radical is "quenched", so it cannot attack and damage any other molecules, such as protein or DNA. In this manner, by absorbing and neutralizing UV radiation and oxygen free radicals, carotenoids protect DNA, proteins, and other crucially important molecules in cells.

These facts about conjugation apply to zeaxanthin and lutein, and they lead to a crucially important difference between zeaxanthin versus lutein, the only two carotenoids that are found in the macula, a crucially-important part of the retina that sits at the very center of the retina. As can be seen by examining their structures, in FIG. 1, the double-bond in the right end ring of zeaxanthin is perfectly conjugated, since it continues and extends the same alternating double-single sequence that appears in the straight-chain portion. Therefore, the semi-mobile "electron cloud" created by the conjugated bonds extends over part of zeaxanthin's right end ring.

By contrast, in lutein, the double-bond in the right end ring is misplaced, and there is no conjugation at all, in the right end ring of lutein. Therefore, one of lutein's end rings has no electron cloud.

It should also be noted, from the chemical structures in FIG. 1, that the other end rings (shown on the left side of FIG. 1) of both zeaxanthin and lutein are identical. In both molecules, the left end rings are conjugated, and have partial electron clouds covering them. This points out another important reason why zeaxanthin appears to be better and more effective than lutein, in protecting human retina cells. Zeaxanthin is perfectly symmetrical, end-to-end. If rotated so that its two end rings swap places, there is absolutely no change. By contrast, lutein is not symmetric, since its two end rings have different structures. If lutein is rotated, it leads to a different alignment, or structure.

That difference between zeaxanthin and lutein (i.e., the misplaced double-bond in one of lutein's end rings) may seem minor, from looking at the chemical drawings in FIG. 1. However, chemical tests have clearly shown that zeaxanthin is more potent and effective than lutein, in absorbing and "quenching" oxygen free radicals. This presumably is one of the reasons why the macula, in human retinas, evolved in a way that clearly favors zeaxanthin over lutein, as described below.

Two other points involving the structures of zeaxanthin and lutein also deserve mention. First, both zeaxanthin and lutein have "hydroxy" (HO—) groups attached to both of their end rings. By contrast, beta-carotene, also shown in FIG. 1, is made entirely of carbon and hydrogen atoms, with no oxygen atoms anywhere.

The fact that beta-carotene is made entirely of hydrocarbon leads to a crucial fact: it is non-polar, which means it is soluble in oily liquids, most of which also are made only of hydrocarbons. By contrast, the presence of hydroxy groups, at both ends of zeaxanthin and lutein leads to a crucially important difference in the way zeaxanthin and lutein behave, compared to how beta-carotene behaves, when any of those three carotenoids, formed in plans, are eaten by animals.

The outer membrane of any animal cell is made of molecules that are oil-soluble at one end, and water-soluble at the other end. These molecules are called phospholipids, since they have a water-soluble "bead" (which contains phosphorous) bonded to an oil-soluble "tail" (made entirely of hydrocarbons). Because of these structures, phospho-lipid molecules will spontaneously line up together, when they are placed in a watery fluid, in a way that gives them a "bilayer" arrangement, shown in FIG. 2A. A layer that contains the water-soluble "heads" of the phospho-lipids line up so that they cover the outside of the cell membrane. This allows the water-soluble "heads" of the phospho-lipids to coat the outermost surface of the cell membrane with a layer that is completely comfortable in the watery liquids that surround the cell (including blood, lymph, and tissue gel). The center layer of the bilayer membrane is made of the oily hydrocarbon tails, which are attracted to each other. The inner surface of the membrane is another layer of water-soluble heads, which will comfortably contact the watery fluid (called cytoplasm) that fills the cell.

Because beta-carotene has an entirely oily structure, made of nothing but oily hydrocarbons with no oxygen atoms or hydroxy groups, it will align itself in a way that causes it to remain fully inside a cell membrane, once it reaches that position. This configuration is shown in FIG. 2B.

By contrast, because zeaxanthin and lutein have water-soluble hydroxy groups at their ends, they will align themselves perpendicular to a cell membrane, in a direction that causes them to "straddle" or "span" the cell membrane. This "membrane-spanning" alignment is illustrated in FIG. 2C.

This crucial difference, in how these carotenoids will align themselves in animal cell membranes, is a major difference between beta-carotene, versus oxygen-containing carotenoids such as zeaxanthin and lutein. Because of how carotenoids and animal cell membranes evolved, in ways that allowed them to survive on earth despite constant bombardment by potentially lethal dosages of ultraviolet radiation from the sun, it is no mere coincidence that most of the oxygen-containing carotenoids (including zeaxanthin, lutein, and various other carotenoids such as canthaxanthin, astaxanthin, etc.) have molecular lengths that allow them to perfectly span the thickness of an animal cell membrane, with their end rings sticking out from both the inner and outer surfaces of the cell membrane.

However, it should also be recognized that this same factor (i.e., the alignment of zeaxanthin or lutein in a direction that causes them to straddle and span an animal cell membrane) makes the difference between the end rings of zeaxanthin, versus lutein, even more important. As mentioned above, both of the end rings of zeaxanthin have conjugated electron clouds that extend into, and cover, parts of both of zeaxanthin's end rings. Therefore, in zeaxanthin, the conjugated electron cloud (which can help absorb and quench UV rays, and oxidative free radicals), extends and protrudes partway out from both sides of an animal cell membrane, when a zeaxanthin molecule settles into the cell membrane.

By contrast, as mentioned above, one of the end rings of lutein has no conjugation, and no electron cloud. Therefore, lutein cannot extend a protective electron cloud, out beyond one side of the cell membrane.

The perfect end-to-end symmetry of zeaxanthin (compared to the lack of symmetry in lutein), and the presence of a conjugated and protective electron cloud over both end rings of zeaxanthin (while lutein has a protective cloud over only one end ring), are presumed to be the primary reasons why the human retina prefers zeaxanthin over lutein.

The retina is the thin layer of nerve cells located at the back of the eye, where sight actually begins. When light enters a mammalian eye, it passes through the cornea (a clear layer on the front of the eye), a clear liquid called aqueous humor (which is thin and watery), a focusing lens (which becomes cloudy, in people with cataracts), and then another clear fluid (called vitreous humor, since it has a consistency close to gelatin). All of those are clear, and they allow light to pass through them, so that the light can reach and activate nerve cells in the retina.

Using "rod and cone" structures that contain light-sensitive chemicals, the nerve cells in the retina convert incoming light, into chemically-driven nerve signals. Those nerve signals are sent to the brain, where they are processed by the brain to form images and sight. Therefore, the retina plays a crucial role in vision. If the retina doesn't work properly, neither does vision.

The macula is the most important part of the retina, by far. It is a small yellowish circle, only about an eighth of an inch wide, located in the very middle of the retina, covering the exact center of the field of vision. However, despite its small size, it is crucially important to good vision, because of a factor most people don't realize. The only part of the retina that provides fine resolution is the macula, in the center of the retina. The rest of the retina provides only coarse resolution.

Most people never notice that fact, because they are accustomed to having both of their eyes flit rapidly across moderately wide areas, in ways that allow the brain to rapidly assemble a complete field of vision with good detail and accuracy. However, the human brain has evolved an extraordinarily useful way to speed up its ability to rapidly make sense of huge numbers of incoming nerve impulses. It does so by using fine resolution only in the very center of the retina, and coarse resolution in the remainder of the retina.

As a simple demonstration of this feature of human vision, if a person cover up one eye, with a hand or sheet of paper, while looking at a page of text, and then looks through just one eye at a single particular letter primed on the page, it becomes nearly impossible to read any of the words directly above or below that letter, in a line of text that is only three or four lines higher or lower on the page. It is also nearly impossible to read any words, through one eye, that are more than about an inch to the left or right of the particular letter that is being stared at. Most people are startled to realize how difficult that challenge is, because they never notice that their vision has fine resolution only in the center.

Indeed, the physical structure of the retinas of primates (which evolved over many millions of years, in ways that helped give primates substantially better vision than other classes of mammals) helped create and drive that feature. In most of a human or other primate retina, the capillaries and other blood vessels that provide blood to the retinal cells (which need large quantities of fresh blood, because they are so active) are placed on the front side of the retina, where they interfere with incoming light. That interference can be tolerated without harming vision clarity, because vision is not very clear or high-resolution anyway, in those parts of the retina. By contrast, in the macula, the structure and placement of the blood vessels is entirely different. In that small region, the blood vessels have moved to the backside of the retina, so that they are positioned behind the layer of nerve cells in the macula. In that one small portion of the retina, they do not interfere with the incoming light before it can reach the retina. Therefore, this placement of blood vessels, behind the nerve cells in the small macular portion of the retina, allows and promotes fine-resolution vision, but only is the very center of the field of vision.

Because it is the only part of the retina that provides vision with fine resolution, the macula must be healthy, for good vision. If the macula degenerates, a person will lose the ability to read, drive, recognize faces, or even be able to walk safely down an unfamiliar sidewalk or hallway.

Los of vision (up to a point that results in functional blindness or major impairments), caused by macular degeneration, happens to hundreds of thousands of people every year. Among the elderly, macular degeneration is the leading cause of blindness. Furthermore, because of demographic and dietary shift in industrialized nations over the past decades (in particular, as the population ages, and as people eat more processed and fatty foods and fewer dark green vegetables), macular degeneration is becoming even more widespread, at alarming rates. As briefly summarized in a newsmagazine, "Eating doughnuts and other fatty treats doubles the risk of going blind later in life" (Shute 2003, which briefly summarized the results reported in Seddon et al 2003). Despite every warning, many millions of people will continue to eat more and more fatty treats, and fewer and fewer dark green vegetables.

Studies of the retinas of people who suffer from macular degeneration (Including studies on living people, using non-invasive measurements of "macular pigment optical density" (MPOD), as well as chemical studies of retinas harvested from macular degeneration sufferers who died of other causes) have made it clear that low levels of macular pigment are strong correlated with increased risk of macular degeneration. It is abundantly clear that people with less-than-normal concentrations of zeaxanthin, in the macular portions of their retinas, suffer higher risks and rates of macular degeneration then people with normal levels of zeaxanthin.

With regard to lutein, there is no clear data, and no clear consensus. Since both pigments normally are found together, in plant sources, it is difficult to distinguish between them, and it generally has been presumed, for nearly two decades, that both pigments are important. However, recent research that has been specifically designed to distinguish between the concentrations and effects of zeaxanthin and lutein has begun to suggest that zeaxanthin plays a more important role than lutein, in protecting the eyesight (e.g., Gale et al 2003).

As briefly mentioned above, another crucially important and revealing fact of nature distinguishes zeaxanthin from lutein, in human retinas. It is clear that the human macula contains only zeaxanthin and lutein, as the two pigments that give the macula its distinctive yellowish color. However, the macula places those two different carotenoids in different locations. It deposits zeaxanthin at highest concentrations directly in the center of the macula, in the most crucial part of the macula. Then, it surrounds that high-concentration zeaxanthin zone in the center, with a ring of higher lutein concentrations.

There is no sharp dividing line, between zeaxanthin in the center of the macula, and lutein around the edges. Instead, there is a transition zone, with zeaxanthin concentrations gradually decreasing, and lutein concentrations gradually increasing, as the distance from the center of the macula increases.

This fact about the retina must be considered in view of an important and well-established fact of nature: lutein is relatively abundant in plant sources, while zeaxanthin is scarce. Lutein is a dominant carotenoid, which is present in a fairly wide variety of food sources. This dominance apparently arose because the structure of lutein's non-conjugated end ring allows it to fit, in an ideal manner, into certain structures in plant cells that are involved in photosynthesis. As a result, even in plants that have unusually high concentrations of zeaxanthin (such a spinach, kale, etc). there is roughly 20 to 50 times more lutein, than zeaxanthin. Therefore, lutein can be obtained much more easily and readily than zeaxanthin, and in much higher quantities and concentrations, from plant sources in the diet.

Nevertheless, despite the huge imbalance in favor of higher lutein supplies, the retina somehow obtains and places the highest concentrations of zeaxanthin directly in the center of the macula, while it places lutein at high concentrations only around the periphery of a zone that has higher zeaxanthin concentrations.

These items of evidence, placed together, strongly indicate that human retinas have developed and evolved with a notable and substantial preference for zeaxanthin, over lutein.

In addition, there is yet another important factor which clearly indicates that the human retina prefers zeaxanthin over lutein. Acting apparently through enzymatic and/or light-triggered reactions that are not fully understood, the human retina attempts to convert lutein into zeaxanthin. However, the retina cannot convert lutein into the same isomer of zeaxanthin that exists in the natural diet. The only isomer of zeaxanthin that is present in dietary sources is the 3R,3'R stereoisomer (also referred to as the R-R isomer, for convenience), which means that the "right" (or dextrorotatory, rather than left, or levorotatory) stereoisomer arrangement is present on both of zeaxanthin's two end rings. However, the human retina cannot form the normal R-R isomer, when it converts lutein into zeaxanthin. Therefore, the retina converts lutein into a different isomer, called meso-zeaxanthin, or S-R zeaxanthin. Therefore, the presence of the non-dietary S-R (meso) isomer of zeaxanthin, in human retinas, is clear evidence that the human retina is attempting to convert lutein, into zeaxanthin.

In passing, it should be noted that the S-R (meso) isomer of zeaxanthin has never been shown to exist in any known dietary sources. Although a report from the mid-1980's (Maoka et al 1986) asserted that meso-zeaxanthin had been found in certain types of fish, that assertion was later contradicted by the discovery that alkaline treatment of carotenoids (as used by Maoka et al) can convert lutein into meso-zeaxanthin. Accordingly, the claim that meso-zeaxanthin had been found in fish may have been, instead, merely an artifact of the carotenoid extraction process they used, and meso-zeaxanthin has never been shown to exist in any food sources that humans eat. Its safety, as a food additive for humans (or as a feed additive for poultry or farm-raised salmon) is not known, and has not been evaluated. Accordingly, any efforts to add meso-zeaxanthin (created by alkaline treatment of lutein) to any human food source (either as a dietary supplement, or as a feed additive that is fed to poultry or fish) raise serious questions as to whether such additives are safe and legal, under the terms of the United States' Dietary Supplement and Health Education Act.

Accordingly, the major points discussed above can be briefly summarized as follows:

1. Zeaxanthin has been shown to be a better and more potent anti-oxidant than lutein, in lab tests;

2. Zeaxanthin is completely symmetrical, while lutein is not;

3. Zeaxanthin is able to extend a "conjugated electron cloud" (which is useful and protective, since it can absorb UV rays as well as destructive oxygen free radicals) beyond both sides of a cell membrane, while lutein can extend that type of protective electron cloud beyond only one side of a cell membrane.

4. Even though lutein is far more abundant in plant sources, zeaxanthin is deposited at higher concentrations in the crucially important center of the macula. Lutein is deposited only at low concentrations in the center of the macula, and at higher concentrations around the less-important periphery.

At one level of analysis, one might presume that these four factors suggest two logical conclusions: (i) the macula wants and prefers zeaxanthin, over lutein; and, (ii) when the macula cannot obtain enough zeaxanthin (because zeaxanthin is so scarce in food sources), it will make up the deficit by using lutein, because of lutein's close structural similarity to zeaxanthin.

However, that is only one possible analysis, and it appears that no one, prior to the inventor herein, has ever cleanly and concisely assembled all four of those factors, into a fully cohesive, consistent, and persuasive argument for zeaxanthin. Instead, any analyses of this invention must also take into account several additional and equally compelling facts and factors, which center around the following:

(i) numerous published reports, in respected and refereed journals, assert that there is no solid and reliable evidence that zeaxanthin actually can help protect the retina;

(ii) numerous published reports explicitly advise physicians who treat patients suffering from eye diseases that it is premature and ill-advised for any physician to instruct patients to begin taking any unproven and potentially dangerous supplements;

(iii) when a large panel of world-class retinal experts was asked, in 1998, by the National Eye Institute, to list the best and most promising candidate agents for future research to help prevent or treat retinal diseases, that entire panel, in its collective wisdom and expertise, completely omitted both zeaxanthin and lutein a candidates that should be considered for research, even though the members of that panel were aware of both zeaxanthin and lutein and had even published articles on them prior to 1998; and, (iv) in October 2003, when one of the world's top experts in treating macular degeneration was informed that one of his patients was taking zeaxanthin, the physician specifically advised the patient to stop taking zeaxanthin, since it might interfere with a different treatment that the physician was planning to give the patient.

These factors offer powerful evidence that the invention disclosed herein, which rests upon zeaxanthin as the crucial and essential ingredient in multi-component formulations for preventing or treating eye diseases, is not obvious to those who are truly skilled in the art, and who in fact have devoted their careers t trying to prevent and treat eye diseases.

This current invention arises from substantial additional readings and research into eye health, by the Inventor herein, during the past several years. Despite his realization that zeaxanthin appears to be the crucial and essential key to good eye health, he continued to carefully study and analyze both: (i) hundreds of published reports and product claims, for literally hundreds of products and ingredients that are being sold or touted as being able to benefit eye health, and (ii) hundreds of published articles, on various aspects of eye physiology, anatomy, and structure, and on eye diseases and disorders.

Those readings and research, followed by extensive thought and efforts to synthesize everything he had read on the subject of eye health and eye products, led him to several realizations that are discussed in more detail below. One of the key realizations can be briefly summarized as follows: the eye is designed to serve as an interface, between two entirely different realms of nature (one realm is outside the body, where light begins, and the other realm is inside the body, where sight begins), and even between two completely different realms of science (the eye must be able to convert physics, in the form of electromagnetic radiation, into chemistry, in the form of neurotransmitters and nerve impulses). The eye can accomplish these results, only by being able to combine, into a single unit, multiple types of tissues, cells, and structures (including two different types of clear tissues, two different types of clear liquids, two different types of photoreceptors, and nearly a dozen distinct layers, in and behind the retina).

One of the factors that enabled and promoted the evolution and development of an extraordinary level of complexity, in human eyes, relates to the fact that carotenoids are multi-functional agents, and can perform more than just one role or task. In addition to being highly effective in absorbing ultraviolet light, they are also highly effective in quenching oxidative free radicals.

However, the multifunctionality of carotenoids doesn't stop there. They also have mild yet potentially helpful and useful ability to control and reduce inflammation. This is a crucial benefit, in many types of eye disorders, since inflammation can lead to severe adverse results, if it lasts for a number of days, weeks, or months in succession. One mechanism for potentially serious damage to the eyesight, cause by inflammation, arises from the effects of increased fluid pressures inside the eyeball. This fluid pressure will be imposed on the exterior surfaces of the capillaries that provide blood to the retina. Since capillary walls must be extremely thin (in order to promote rapid exchange of oxygen, nutrients, and metabolites), they cannot resist and push back against elevated fluid pressures on their exterior walls. As a result, elevated pressures inside the eye, if they arise as a result of inflammation after an injury or infection, can act in a manner comparable to a severe and accelerated case of glaucoma (a disease that also involves elevated fluid pressures inside the eye, which causes reduced blood flow through the retinal capillaries, and which can cause severe and permanent damage to retinal nerve cells). Therefore, the ability of certain carotenoids to help control and reduce inflammation can become crucially important, and extremely helpful, in response to injuries, infections, or other events that can trigger inflammation of one or more types of eye tissues.

Similarly, carotenoids also have a mild yet potentially useful and helpful level of activity in preventing and reducing "sclerosis". This term refers to hardening, stiffening, and loss of flexibility (for example, arteriosclerosis refers to hardening of the arteries, and atherosclerosis is a related process in which the insides of the arteries become coated with cholesterol or other fatty deposits). In the eyes, sclerosis and loss of flexibility (which can also arise when substantial quantities of drusin, lipofuscin, and other debris accumulate) can adversely affect certain membranes, such as the Bruch's membrane, which is a crucially important layer in the back of the eye, behind the retina. Therefore, the ability of carotenoids to help prevent and reduce sclerosis is yet another way in which carotenoids can help protect eye health and good vision.

After the inventor herein had read about and recognized those additional roles of carotenoids, he then began to actively notice still more different roles and activities that are being played by carotenoids. A complete list must include (but is not limited to) the following:

(1) Carotenoids have mild yet potentially useful levels of activity in controlling and regulating angiogenesis (i.e., the formation of new blood vessels, which can lead to extremely severe problems in the wet or exudative form of macular degeneration).

(2) Carotenoids have mild yet potentially useful levels of activity in helping to modulate and regulate the functioning of mitochondria, which are crucial to oxygen usage, respiration, and energy utilization by a cell.

(3) Carotenoids have mild yet potentially useful levels of activity in helping to modulate and regulate apoptosis, a form of "programmed cell death," in which cells that receive certain signals or that enter into certain states trigger a process that leads to fairly rapid death of the cell. This process effectively allows other specialized cells (glial cells in the nervous system, and immune cells in the remainder of the body) to clean up and remove the cell debris, so that the system in that locality can go back to functioning properly, without being hindered by a lingering cell that is crippled, useless, and a drain on resources.

(4) Carotenoids have mild yet potentially useful levels of activity in helping to regulate and control certain types of actions and responses of the immune system.

It must be kept in mind that this brief listing (immediately above) of four different "peripheral" activities, by carotenoids, must be added to two other peripheral activities (i.e., modulation of inflammatory responses, and modulation of sclerotic hardening), and all six of those activities must then be added to the two "primary" activities of carotenoids (i.e., absorbing and quenching destructive ultraviolet photons, and absorbing and quenching destructive oxygen free radicals).

There are also various other scientific reasons for believing that (i) many eye disorders are multi-factorial, and (ii) the best treatments or preventive agents for such disorders will also be multi-factorial. These factors are highly complex, and involve, for example: (i) the fact that inflammation and immune responses can both create oxygen free radicals and "reactive oxygen species"; (ii) various types of signalling pathways that cells use, to effectively communicate with each other; and (iii) the crucial involvement of mitochondria in many of these processes, and in processed involving apoptosis and programmed or signalled cell death.

Upon reading and realizing that carotenoids must be able to perform two absolutely crucial primary and central roles (neutralizing UV photons and free radicals), while also being called upon to perform at least six known secondary and peripheral activities, the inventor herein gradually reached several conclusions about carotenoids in human eyes. Those two conclusions can be summarized a follows:

1. If carotenoids are being asked to perform eight different tasks (and possibly even more) in a single eye, they are more likely to become "stretched thin", and unable to adequately handle all of those tasks simultaneously, than other molecules that only need to perform fewer numbers of tasks;

2. Research reports have indeed shown that people who are suffering from certain types of eye problems do indeed suffer from low carotenoid concentrations in their blood (as shown by tests on blood serum) and/or their eyes (as shown by inadequate levels of zeaxanthin in people with macular degeneration, and reduced zeaxanthin densities in the lenses of people suffering from cataracts);

3. If any or all of the "secondary demands" that are being imposed on carotenoids in the eyes can be reduced, by ingesting or administering other nutrients that can provide a balanced regimen that will help address and satisfy those secondary demands, then any newly-arriving carotenoids will be more likely to actually arrive at locations where they can carry out their essential primary roles, and provide the most overall benefit.

Accordingly, over a span of time that allowed careful consideration and additional readings on related subjects, this line of logic and analysis began to suggest, more and more persuasively, that well-balanced eye-care preparations would be able to do the greatest possible good, in protecting or restoring the extraordinarily complex needs of human eyes, if those formulations contain both: (i) zeaxanthin, as the ideal, symmetric, fully-conjugated carotenoid that has been fully optimized (by millions of years of evolution) for interacting in beneficial ways with animal cells and animal cell membranes; and, (ii) one, two, or more additional ocular-active nutrients that can directly and efficiently address and correct any one or more "secondary demands", which otherwise will tend to "siphon off" part of any zeaxanthin that reaches the eye.

Viewed from another perspective, zeaxanthin can be regarded as a form of "buffer", in a system that is constantly trying to sustain an equilibrium (which is usually called "homeostsis", when living biological systems are involved). Like buffer compounds, carotenoids can respond to whatever is added to (or imposed upon) the system, in a way that usually will help the system move back toward its equilibrium (also referred to as the "set-point" of the system). However, it must also be recognized that if the outer limits of the buffering capacity of a certain buffer compound has been reached in a certain system, addition of even a slight quantity of additional acid or alkali can cause major swings and unheavals, in the system. In an analogous manner, if the carotenoids in a human eye are "stretched thin", by a combination of multiple competing demands, all demanding responses at the same time, then the overall protective system can fail, leading to a variety of stresses, problems, and damage, all occurring at once, and acting together in ways that are suggested by phrases such as vicious circle, witch's brew, etc.

Subsequently, as the inventor pondered various approaches to developing and optimizing ways to respond to complicated and intertwined problems that lead to (or are caused by) complex, difficult, and often intractable ocular diseases and disorders (which lead to serious visual impairment, functional blindness, or complete blindness in millions of people every year, despite the best efforts of thousands of doctors and researchers), he eventually arrived at a complex intersection, where roughly half a dozen distinct themes all converge and cross each other. Briefly, those themes include the following:

(i) Using nature and evolution as the best examples and the best instructors, many and probably most of the best candidate ocular-active nutrients are likely to be derived from plants;

(ii) In the same way and for the same reasons that occur in plants, many and probably most of the best candidate ocular-active nutrients are likely to have strong or even exclusive specificity for certain stereoisomers, and racemic mixtures created by non-specific chemical synthesis should be avoided wherever possible;

(iii) Despite the dominance of plant nutrients as offering the best candidates overall, humans evolved most efficiently as omnivores, and diversity should be recognized, respected, and valued. Accordingly, animal sources may well offer one or two ocular-active nutrients that may provide good and useful complements, when added to best-candidate plant nutrients for eye health; and, (iv) after a list has been developed that contain the best candidates from the realm of naturally-occurring ocular-active nutrients, the final step is to make good, shrewd, intelligent use of technology, to get those natural products properly stored, packaged, and delivered. In this context, appropriate technological steps can include, for example: (i) the use of oily carrier substances, to deliver active agents (including carotenoids) that are naturally oil-soluble; (ii) the use of timed-release and/or sustained-release technology, to establish sustained and lasting increased blood concentrations of any compounds that otherwise disappear rapidly from the gut or from circulating blood; and, (iii) the use of various types of bioavailability enhancers (such as bile salts, phospholipids, or pancreatic lipase), to increase the uptake of oily compounds through the Intestinal walls, and into circulating blood.

After extensive thought, reading, research, and discussions concerning various different factors listed above, the inventor herein has reached a point where it is now time to convert these concepts and ideas into detailed and specific tests, which must be woven together into a consistent and cohesive program that is planned and organized to lead directly to a specific outcome that can be clearly envisioned and described at this time, even though the screening tests have not yet been commenced that will identify those specific agents that will perform most potently, synergistically, and beneficially, when combined with zeaxanthin.

Accordingly, one object of this invention is to disclose multi-component orally-ingestible formulations for protecting eye health in mammals (including humans), which contain zeaxanthin as an essential and critical ingredient, and which also contain at least two or more other agents that have been proven, in tests on humans or other primates, to act in a synergistic and potentiating manner with zeaxanthin to provide improved efficacy in preventing or treating eye diseases.

Another object of this invention is to disclose a focused method of approach that will be able to clearly identify ocular-active nutrients that, when added to zeaxanthin, will be able to improved the efficacy of zeaxanthin in preventing or treating eye diseases.

Another object of this invention is to disclose a method (which has intertwined aspects of both scientific research, and a method of doing business) that will sort through hundreds of competing and confusing products that are accompanied by unsupported and unreliable advertising and marketing claims, and which will provide (i) elderly people who are suffering from vision loss; (ii) their families, caregivers, and insurance companies; and, (iii) government and charitable institutions that will be forced to bear the brunt of the costs of caring for millions of elderly people who are at severe risk of becoming functionally blind, with genuinely useful and reliable products and information that will be truly effective in preventing an epidemic of blindness, which otherwise will occur as the population ages, and a the long-terms effects of unhealthy high-fat diets gradually take their toll on the aging populace.

These and other objects of the invention will become more apparent, through the following summary, description, and claims.

SUMMARY OF THE INVENTION

A process is disclosed for identifying ocular-active nutrients that will interact in a synergistic and potentiating manner with a carotenoid called zeaxanthin, to provide better and more effective protection, for eye health, than can be provided by zeaxanthin alone. Product-by-process combinations of such ocular-active nutrients that are identified as offering especially potent and useful eye health benefits, when combined with zeaxanthin, are also disclosed.

Eight categories of candidate ocular-active nutrients are identified herein. These eight categories can be summarized as follows:

(1) Lipoic acid, preferably in the form of a purified or enriched naturally occurring "R" (dextrorotatory) stereoisomer rather than a racemic mixture.

(2) At least one omega-3 fatty acid, such as docosohexaenoic acid (commonly referred to as DHA) or one of its linolenic acid precursors, preferably obtained from a natural source such as fish oil or marine algae.

(3) Various plant-derived compounds that are referred to by various scientists as flavonoids, bioflavonoids, anthocyanins, plant polyphenolics, or phytonutrients. These compounds include extracts from bilberry, grapeseed, or green tea, as well as soy isoflavones, quercetin, genestein, diazedem, fisetin, luteolin, resveretrol, and pycogenol.

(4) Taurine, the common name for amino-ethane-sulfonic acid, a "conditionally essential nutrient" that is present in milk and various tissue types.

(5) Carnitine, a sulfur-containing amino acid (not one of the 20 primary amino acids used in protein synthesis) that is formed in the liver and elsewhere, and various esters and/or precursors of carnitine, such as acetyl-L-carnitine.

(6) An enzyme cofactor known as Coenzyme-Q10, which is a known anti-oxidant that provides energy-related support to mitochondria. In some situations, it can help prevent or reduce a process called "apoptosis" that leads to a type of programmed cell death.

(7) Carnosine, a di-peptide formed from alanine and histidine, which can prevent reactive aldehydes from causing unwanted glycosylation or crosslinking of proteins.

(8) Nutrients that can stimulate the production or metabolism of glutathione, a tri-peptide that helps cells eliminate waste products. One such agent is N-acetyl cysteine, an ester that is metabolized to release the cysteine, the sulfur-containing amino acid in the center of glutathione.

In addition to those eight categories (none of which were tested during the AREDS-1 trial in the 1990's), three classes of compounds that were tested in the AREDS-1 trial also may merit attention. Two of those categories include tocopherol compounds, such as alpha-tocopherol (vitamin E), and ascorbic acid (vitamin C) or a salt or ester thereof, such as ascorbyl palmitate. The third category includes zinc. When vitamins C and E (as well as beta-carotene) were combined at high dosages, they offered a low and weak level of protection against macular degeneration, in some but not all of the patient categories, in the AREDS-1 trial. Similarly, zinc at very high dosages (80 mg/day), by itself, offered a low and weak level of protection in some categories of patients. When vitamins A/C/E and zinc were combined, the level of protection increased, especially among late-stage macular degeneration sufferers.

Accordingly, the results and findings of the AREDS-1 trial are not regarded as strong or compelling, when compared with the potential benefits of zeaxanthin, and in recent years it also has become clear that high dosages of vitamin A or its precursor, beta carotene, offer little or no serious hope for providing any significant protection against macular degeneration, or any other serious eye disorders among people who receive minimal baseline levels of vitamin A. However, various general and specific benefits of vitamins C and E, and of zinc, are well known and solidly proven, especially among elderly people and people with poor diets. Therefore, vitamins C and E, and zinc, remain of interest, and they will be tested (possibly in the form of the complete AREDS formulation, which is commercially available) in combination with zeaxanthin, to determine whether they can provide a synergistic benefit that will improve substantially on the results that can be provided by zeaxanthin alone.

To evaluate and rank the efficacy and synergistic activities of these candidate ocular-active nutrients, selected tests that have been chosen to accommodate various animal models (including a number of animal models described below) can be used. Each type of animal model can provide different types of data, which will relate to certain components of the eye and certain known ocular disorders. Researchers who are experienced in designing and carrying out such tests understand the types of data that can be gathered from each such test, and from each type of animal species that is well-suited for use in a particular type of test. Accordingly, testing regimens with targeted data-gathering methods can be developed, to gather specific types of data that will indicate which ocular-active nutrients listed above are likely to have the most valuable and beneficial effects, when combined with zeaxanthin and then tested in human clinical trials.

Based on the results of the animal tests, candidate formulations can be tested in clinical trials on humans who are suffering from various types of eye disorders. Testing regimens are known, and can be designed by skilled experts, for use with nearly any type of eye disorder. At least some types of tests can be designed to speed up the gathering of useful data, when testing patients suffering from diseases that gradually manifest over a span of multiple years. This type of accelerated data gathering can be enabled by various approaches, such as by focusing on selected patients who, at the point in time when they will be tested, are entering or progressing through certain stages that involve accelerated and rapid degeneration and loss of vision acuity. One example, among moat patients who suffer from the dry form of macular degeneration, involves an intermediate stage called "geographic atrophy", which occurs when distinct patches of degeneration in or around the macula become clearly visible, in certain types of diagnostic photographs. It is not yet known which specific ocular-active nutrients in the candidate categories listed above will act in the most potent, effective, and beneficial synergistic manner, when combined with zeaxanthin. What is known, instead, is that the uncontrolled and unsupported profusion of eye-care nutritional products, all with their own competing and confusing claims designed to sell products now (rather than support research for the future), is not working adequately, and will not work adequately in the future, unless something happens that alters the landscape in an important and useful manner. Patients cannot be sure what to take, physicians cannot be sure what to recommend, and the largest and most powerful companies that sell eye care nutrients have shown, by their actions, that they apparently are determined to minimize zeaxanthin in their plans and products, rather than recognizing its crucial role at the center of the macula, and as the foundation and the single most important ingredient in any nutrient formula that will be truly effective and useful in protecting eye health and good vision.

The current system does not offer any realistic hope of preventing dozens or even hundreds of millions of cases of avoidable blindness, which will occur around the world over the next 20 years unless a better approach can be found than the approach that has been adopted and used so far by the largest companies that sell eye care products, and by the National Eye Institute. Accordingly, the testing and screening approach disclosed herein should be regarded as a process, and the synergistic compositions that will result will be product-by-process compositions. Such product-by-process compositions should be evaluated, not by pointing out that certain Items of prior art have been published on each of the candidate nutrients listed above, but by comparing the testing and screening method disclosed herein, which will treat zeaxanthin as an essential "anchor" ingredient that will be included in all formulations that will result from this approach, against: (i) the research programs and eye-care nutritional products that have been created by other companies that sell such products; and, (ii) the actions of the National Eye Institute, which has stated in communication to the inventor herein that it is planning to deliberately exclude zeaxanthin from the so-called "AREDS-2" trial, and focus on lutein instead.

BRIEF DESCRIPTION OF THE DRAWINGS

FIG. 2A depicts the way a molecule of bets-carotene (which has no oxygen atoms or hydroxy groups) will aligned itself entirely within the oily interior of a cell membrane.

DETAILED DESCRIPTION

Figure 1:
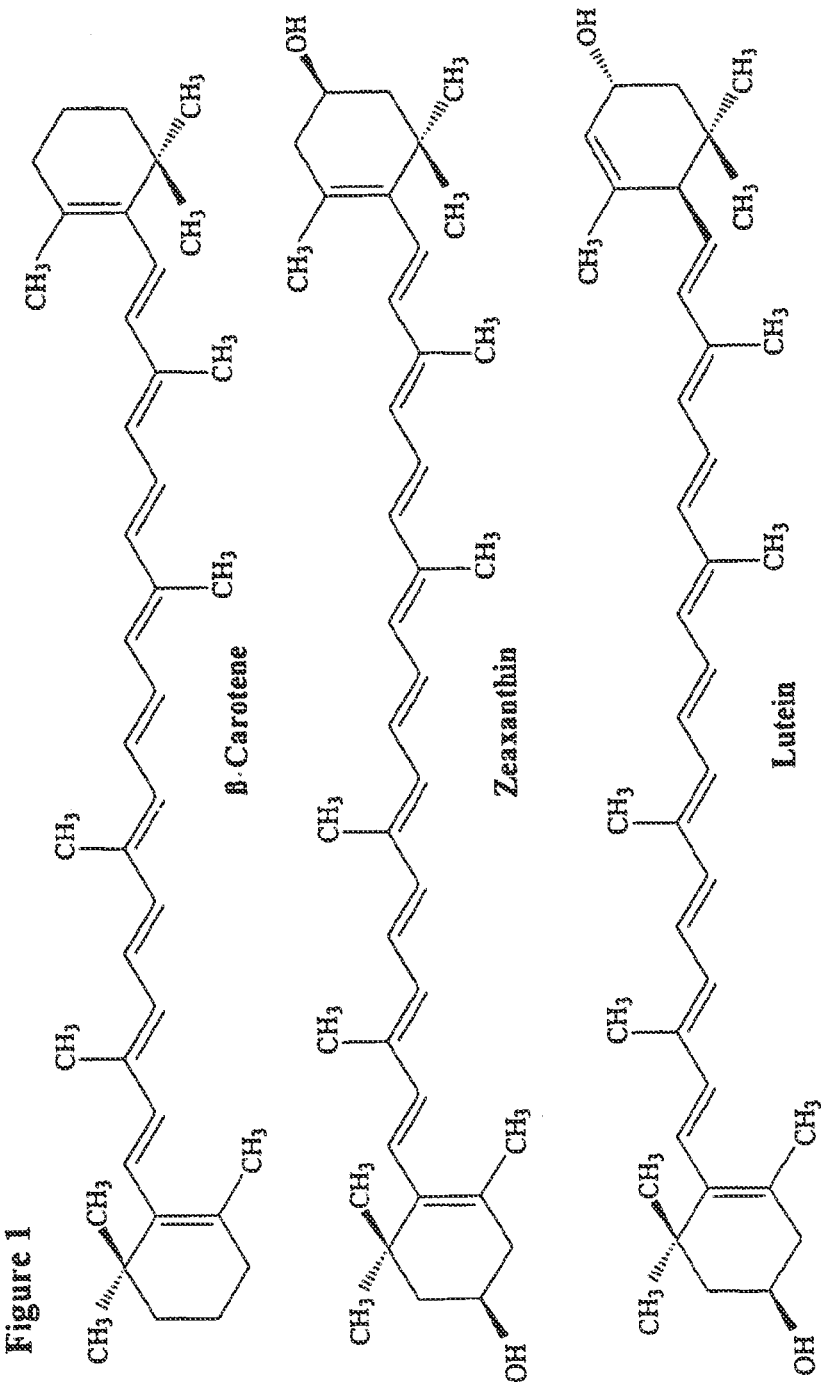
FIG. 1 (which is prior art) depicts the chemical structures of zeaxanthin and lutein (with an arrow pointing out the misplaced non-conjugated double bond in one end ring of lutein), and beta-carotene (a similar carotenoid that does not contain any oxygen molecules or hydroxy groups).
Figure 2A:
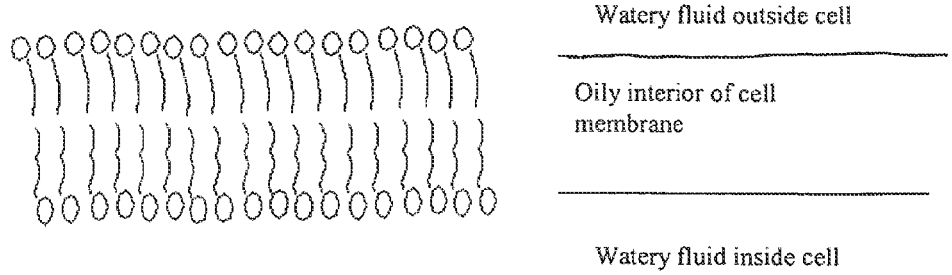
FIG. 2A depicts the bilayer structure of an animal cell membrane, formed by two rows of phospho-lipids having water-soluble phosphate "heads", and oil-soluble lipid "tails".
Figure 2B:
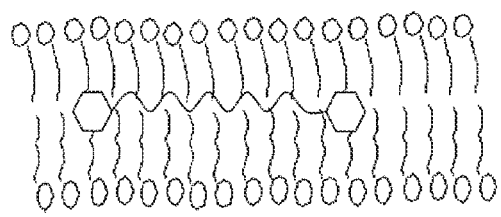
FIG. 2B depicts how molecules of zeaxanthin and lutein will align themselves to "span" or "straddle" a cell membrane, in a way that causes their end rings and hydroxy groups to protrude and extend out, beyond the cell membrane's outer and inner surfaces.
Figure 2C:
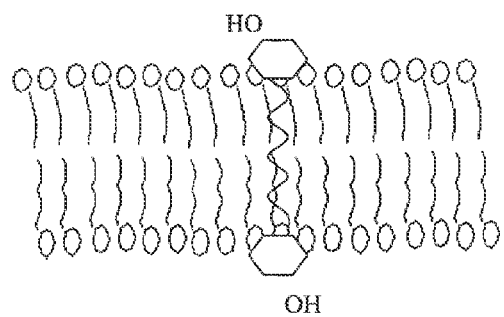
FIG. 2 (which is prior art) comprises FIGS. 2A, 2B, and 2C.

As briefly summarized above, this invention relates to "ocular-active nutrients" that can act in a synergistic and potentiating manner with zeaxanthin, to protect and/or restore eye health and good vision to a degree that rises substantially above the levels of benefit that can be provided by zeaxanthin alone.

Several points of terminology need to be addressed, before describing the testing and screening method, and the categories of candidate nutrients, in more detail.

Ocular relates to the eye, and terms such as ocular-active can be used interchangeably with other terms such as ophthalmic, eye-related, vision-related, etc.

The term nutrients, as used herein, refers to compounds that are found in the normal human diet. Under the various laws that have been passed to regulate foods and drugs, nutrients that are present in normal human diets are usually covered by the laws and rules of the U.S. Dietary Supplement Health and Education Act. By contrast, drugs and pharmaceuticals that are not found in the normal diet are regulated separately, under different statues and rules. However, as mentioned below, it should also be recognized that some nutrients found in the normal diet can be regarded and regulated as drugs or pharmaceuticals, if (and to the extent) they are prescribed by physicians to treat specific and diagnosed medical conditions.

Ocular-active nutrients, as used herein, refers to and is limited to compounds developed for oral ingestion, to provide active, substantial, and measurable benefits for one or more aspects of eye health or vision quality. Although some of these nutrients may also be useful (and indeed might have accelerated effects) if administered by other means (such as by intravenous or intraocular injection), all claims herein are limited to nutrient formulations that are intended to be ingested orally. This is deemed to be the relevant field of art and usage, and published art on other, different types of formulations (such as, for example, injectable drugs) are not deemed to be relevant herein.

The major use for orally-ingestible ocular-active nutrients, as discussed herein, is to protect or treat human eyes, and vision. However, if desired, such formulations may also be used to prevent or correct eye-related problems in other mammalian species, such as to prevent cataracts or retinopathies in dogs. The combined formulations of this invention can be in the form of pharmaceutical preparations, dietary supplements (also referred to interchangeably as nutritional supplements), or foodstuffs.

Pharmaceutical preparations (which can be prescription-only, over-the-counter, or any combination of the two) normally are used to treat known and already-existing problems, while dietary supplements (also referred to interchangeably herein as nutritional supplements) normally are used to sustain a condition of good health. While there is no clear dividing line between pharmaceutical preparations versus dietary supplements (for example, treating physicians often recommend dietary supplements to patients who are suffering from specific diagnosed problems), a practical difference nevertheless exists between the two categories. This arises from the fact that pharmaceutical preparations usually contain higher dosages of active agents, than dietary supplements. Accordingly, for purposes of discussion and description herein, terms such as "pharmaceutical preparations" and "therapeutic dosages" are deemed to include any combinations of ocular-active nutrients, as discussed herein, that contain at least 3 milligrams (mg) of zeaxanthin, either as a unitary dosage, or as a recommended daily dosage. Preferred therapeutic dosages for most patients who are suffering from diagnosed eye disorders usually will comprise 10 or more mg of zeaxanthin per day.

Dietary (nutritional) supplements generally comprise formulations and preparations that are designed to be taken by people who wish to sustain a condition of good health, or at least to prevent any further deterioration of their health, regardless of whether they have been diagnosed with a particular disorder by a physician. Accordingly, dietary supplements they usually have unitary and/or daily dosages that are within a range that is (i) higher than the minimal quantities (often called "trace amounts") that are contained in naturally occurring foods, but (ii) lower than the therapeutic dosages that are provided by drugs and pharmaceuticals that are used to treat known medical problems. Accordingly, for purposes of discussion and description herein, dietary (nutritional) supplements are deemed to include preparations that contain at least about 0.5 mg zeaxanthin, as either a unitary dosage, or as a recommended daily dosage.

As mentioned above, the categories of pharmaceutical preparations and dietary (nutritional) supplements overlap, and there is no specific upper limit for dosages that would cause a dietary (nutritional) supplement to be reclassified as a pharmaceutical preparation. Safety data that was gathered on zeaxanthin, using high-dosage tests involving rats, indicated a "no adverse effect limit" (NOAEL) level of at least 1200 mg/day. These data were disclosed in a "75-day Premarket Notification" for zeaxanthin, which was submitted to the U.S. Food and Drug Administration (FDA) by Roche Vitamins, Inc. (the only company that is currently manufacturing the R-R dietary isomer of zeaxanthin, for human consumption), and which was opened for public inspection by the FDA in June 2001 under FDA number 95S-0316. In addition, small-scale tests involving human volunteers indicated that dosages of zeaxanthin in a range of 50 to 80 mg/day appear to be entirely safe, and were effective in reducing a person's risk and severity of sunburn, when small areas of skin were exposed to controlled dosages of high-intensity ultraviolet radiation from a medical-grade UV lamp. These high dosages of zeaxanthin also succeeded in creating slightly reddish skin tones, which turned a darker brown or bronze color that completely resembled a healthy tan, when subsequently exposed to the sun. Accordingly, people who want tans, or who are planning to go on a vacation or other trip that will involve exposure to abnormally high levels of sunlight, may take large quantities of zeaxanthin (up to or even exceeding 100 mg/day), to help them avoid sunburn and obtain a deeper tanned color on their skin. Such use, even at very high quantities, would be regarded as taking a dietary supplement rather than a pharmaceutical, and such dosages would still remain far below the NOAEL levels that were determined by animal tests.

On the subject of unit dosages and daily dosages, unit dosage forms involve discrete units. The most common forms are capsules (which use an encapsulating material), tablets (which use compressible binder materials), and various types of "hybrid" pills that use encapsulating materials as well as compressible binders (usually called caplets, coated tablets, etc). Other types of unit dosages can also be provided by other means, such as sealed plastic pouches containing measured amounts of a powder or liquid that is to be added to a food or drink.

Daily dosage forms can include unitary dosage forms (such as tablets or capsules, which normally are accompanied by a recommendation to take a specified number of pills per day to achieve a recommended daily dosage). Daily dosage forms also can include liquids, powders, or similar preparations, which usually are accompanied by instructions concerning a certain volume, weight, or other quantity that should be ingested each day to achieve a recommended daily dosage.

It should also be noted that unit dosages can be provided in the form of capsules that will contain oily carrier materials, such as a vegetable oil. This can enhance the uptake and bioavailability of zeaxanthin, vitamin E, and various other oil-soluble nutrients disclosed herein. If desired, such oily carriers can also be formulated to carry microencapsulated beadlets or other preparations, which can contain water-soluble nutrients or any other components that are easier to handle if isolated or otherwise coated in that manner.

Another class of compounds that can contain zeaxanthin combined with other ocular-active agents is referred to herein by the term "foodstuffs". This broad industry term includes compounds that are designed to be eaten as a food or drink, having enough volume and bulk to help satisfy an appetite or thirst (as distinct from a tablet, capsule, or other low-volume drug-type preparation). Foodstuffs can be complete and ready to eat (such as snack foods, energy or nutrition bars or mixes, or desserts, or beverages that are sold in cans, bottles, or pouches, etc.); they can require cooking, mixing, or other preparation (such as frozen or refrigerated snacks or entrees, soups or other foods sold in cans or pouches, cooking ingredients, drink mixes, etc.); or, they can involve any combination of or midway point between those categories (such as peanut butter, cheese, vegetable dips, cracker spreads, etc.). They also can be in the form of condiments (such as ketchup, sauces, butter, margarine, etc.), flavoring or coloring additives, or any other preparations that are designed and intended to be added to foods or beverages, or otherwise eaten or drunk as a food or beverage.

In order to be covered by this invention, say such foodstuff must contain zeaxanthin and at least two or more other ocular-active nutrients, not merely as naturally-occurring ingredients in one of the fruit, vegetable, or other materials used to make the foodstuff, but as additives that were deliberately added to the foodstuff, in a quantity intended to provide ocular benefits to consumers. In most cases, this type of intent will be made clear and explicit by labelling information on packaging, advertising, or other marketing materials that advertise, enclose, or otherwise accompany the foodstuff, which will claim or suggest that an ocular benefit can be provided by the foodstuff or the additives therein. Advertising and labelling is an essential part of identifying and marketing foodstuffs having special health-related benefits, since the additional costs of such agents cannot be justified unless consumers know about the added benefits and are therefore willing pay a correspondingly higher price for products containing them.

The benefits of ocular-active combinations as disclosed herein may include preventing, treating, or reducing the risks of any one or more eye diseases, injuries, or infections or other eye-related and/or vision-related problems. Such eye-related or vision-related problems include, for example, retinal problems such as macular degeneration, retinitis pigmentosa, and diabetic or other retinopathies; lens-related problems, such as cataracts (including cataracts relating to diabetes); fluid-related problems, such as glaucoma, "dry eye" syndrome, tearing problems, etc; problems related to hypersensitivity to light, as occur in people with albinism, or who suffer from headaches, epileptic seizures, or other disorders when exposed to certain types of light; and undesired effects or problems arising from injury or infection, or from a surgical or medical procedure that directly affects one or both eyes of a patient or animal (such as a vitrectomy, repair of a torn or detached retina, laser coagulation using verteporfin, etc.). These and various other eye-related disorders are known to ophthalmologists and other specialists.

While there is no specific reason to believe the treatments herein can prevent, retard, or reverse focusing problems that are normally corrected by glasses (near-sightedness, far-sightedness, or astigmatism), such focusing problems may be aggravated and increased, in at least some patients, by other types of stress or damage imposed on the eye. As an illustration of this principle, eye-related disorders frequently are accompanied (and brought to the attention of a patient or physician) by unusually rapid changes in the corrective strengths that must be provided by eyeglasses or contact lenses. Accordingly, by establishing better, more stable, and healthier overall conditions in the eye, the tremens herein may be able to help retard the onset of, or reduce the need for, lens correction.

It also should be noted that corrective lenses (including bifocal lenses, etc.) are the standard treatment for presbyopia, which refers to the decline in vision acuity that, in most people, commences or accelerates in middle age. It is believed and anticipated that, in at least some patients, by improving the general health of the eyes, by reducing oxidative damage within the eyes, and by reducing stresses imposed on various components of the eyes, the nutrient formulations of this invention can help delay the onset of presbyopia, and/or reduce its severity, especially if taken over a span of years.

As used herein, terms such as treat, treatment, therapy, or therapeutic are used broadly, and include the ingestion or administration of pharmaceutical preparations, dietary or nutritional supplements, or foodstuffs with additives as disclosed herein, in an effort to respond to an existing and known ocular disorder (which can include a disease, injury, infection, etc.). Such treatments may retard or delay, fully or partially reverse, or otherwise ameliorate, lessen, or benefit a known ocular disorder. Such problems, when they arise, may be revealed by an ophthalmic examination, vision test, or other medical examination, or they may simply become apparent and troublesome to a sufferer (such as a noticeable loss of clear vision). Such disorders may become known, even though the sufferer or a treating physician may not have an accurate diagnosis and may simply be aware that something is wrong with either or both eyes or the vision of the sufferer.

As used herein, terms such as preventing or prophylaxis also are used broadly, and include the ingestion of pharmaceutical preparations, dietary or nutritional supplements, or foodstuffs with additives, either (i) to sustain a general state of good health and/or good vision, and/or to reduce a general risk of health or vision problems, in a manner comparable to taking vitamins; or, (ii) in a manner that is intended to reduce a known elevated risk of one or more ocular diseases or disorders, by someone with a family or personal history of a disease or disorder, a known or suspected genetic defect, or some other factor that indicates an elevated risk of one or more ocular disorders.

Just as there is no clear dividing line between vitamins and drugs (for example, a vitamin becomes a drug when it is used to treat someone suffering from a known vitamin deficiency), there is no clear dividing line between preventive versus therapeutic usage of ocular-active nutrients as discussed herein. As an example, if someone who is relatively young suffers from a known genetic defect that will affect his or her vision later in life, and if that person begins to regularly take an ocular nutrient formulation before any specific degeneration becomes apparent, then such usage by that person can be classified either as preventive (since the nutrients are being taken to prevent, delay, or reduce problems that have not yet arisen), or therapeutic (since the nutrients are being taken to treat a known genetic defect that already exists).

Accordingly, while it is useful to bear in mind that this invention relates to both pharmaceutical preparations (intended for treating known problems, and typically involving high dosages) and dietary/nutritional supplements (intended to sustain eye health, and commonly but not necessarily involving lower dosages), those two categories sometimes overlap and/or merge with each other, and are not entirely separate and distinct from each other. It should also be recognized that the category of foodstuffs containing ocular-active additives, as described above, normally will fall within the category of dietary or nutritional supplements, but may be regarded as pharmaceutical and therapeutic, when ingested by someone who is suffering from a known ocular problem.

While it is not claimed that any one particular ocular-active formulation can be used to effectively treat all eye-related disorders, the following points are asserted by the inventor:

(1) Because of the central role that zeaxanthin plays in the eye, in absorbing and quenching ultraviolet radiation as well as oxidative free radicals, nutrient formulations that contain zeaxanthin along with other ocular-active nutrients are highly likely to be substantially more effective, in treating a wide variety of eye disorders, than comparable formulation that do not contain zeaxanthin; and, (2) Any well-planned, useful, and publicly and socially helpful research project that is intended to help create or evaluate a useful and beneficial ocular-active nutrient formulation must be designed to evaluate candidate agents, not in isolation, but in combination with zeaxanthin, since zeaxanthin will be an essential ingredient in any optimal or near-optimal nutrient formulation that will truly benefit and protect the vision of as many people as possible.

Animal Models For Initial Testing

As mentioned above, at least five different and distinct animal models are known, for testing candidate ocular-active nutrients. These models include the following:

1. Mice and Rats, Including "Knockout" Mice

Mice and rats are very widely used in research on small animals, and a huge foundation of Information, species-specific biomolecules (including gene promoter sequences, gene coding sequences, monoclonal antibodies, etc.) and specialized strains have been developed for genetic work with mice. Gateways that can be used to access mouse genetic information are freely available on websites such as www.informatcs.jax.org and www.ncbi.nlm.nih.gov/genome/seq/MmHome.html. Although the corresponding genetic information on rats is somewhat smaller, it is still enormous and quite useful, and can be accessed through websites such as http://rgd.mcw.edu, http://ratmap.gen-.gu.se, and www.hgsc.bcm.tmc.edu/projects/rat.

This genetic information can be put to good use, because a growing number of gene defects have been and are being correlated with known eye disorders. These genes can be discovered by any of several procedures. For example, research revealed that many people who suffer from Stargardt's disease, which causes severe vision impairment, have a defective protein known as the Rim protein, which normally functions as an ATP-binding cassette (ABC) transporter gene, in rod outer segment discs, in mammalian retinas. Additional research on that protein (and the gene which encodes that protein) led to identification of a gene called the ABCR gene, as the specific defect that leads to the defective Rim protein in people who suffer from Stargardt's disease.

After the human ABCR gene was identified as a causative factor in Stargardt's disease, a "homologous" ABCR gene in mice was located, which encodes the mouse version of the Rim protein. The exact DNA sequence of the mouse ABCR gene was determined, and researchers then used genetic engineering techniques to create mutant mice with "knockout" ABCR genes that are no longer properly functional. These mutant mice, with "knockout" ABCR genes and the mouse equivalent of Stargardt's disease, are described in articles such as Weng et al 1999 and Matsa et al 2000. Their descendants suffer from severe visual impairment, which grows gradually worse as certain waste metabolites gradually accumulate within the retinas. Therefore, the descendants of these knockout mice offer useful animal models, for testing candidate nutrients that may be able to help slow down the gradual loss of vision in such mice.

This example, focusing on the ABCR gene that was rendered nonfunctional in a colony of "knockout" mice, is just one of numerous examples of how rapid progress is being made, by using and comparing gene sequence information that has already been gathered as part of the human genome project, the mouse genome project, and the rat genome project. Dozens or even hundreds of genes that express specific proteins involved in eye structures and/or vision processing have been identified, and the only things that limit how quickly and effectively that genetic information can be used are money, and resources.

Four presumptions apply to such research: (1) every structural protein that is present in any eye structure, and every enzymatic protein that is involved in any step in vision processing in the eyes, is present within the eyes for a good reason, and plays some useful and necessary role in vision; (2) a gene defect that renders any such protein nonfunctional will very likely lead to some type of identifiable and potentially important eye disorder; (3) once any such genetic defect has been identified, either in humans or in mice or rats, colonies of lab animals which will carry that genetic defect can be created and/or raised; and, (4) any such colony can provide an animal model, which can help researchers evaluate and rank the ability of various candidate nutrients or other treatments to overcome the problem that is caused or aggravated by that particular defective protein, in that particular animal model.

Accordingly, genetic analysis and research, including research involving mice or rat colonies having "knockout" genes that are correlated with specific vision disorders, offer extremely powerful tools, and can provide an effectively unlimited amber and range of specific targeted "models" that can help researchers test candidate nutrients, to evaluate whether any nutrient or nutrient combination can act synergistically with zeaxanthin, to help prevent or treat one or more specific types of ocular disorders.

2. Use of Agents to Increase Carotenoid Uptake in Rodents

When carrying out vision-related research on mice or rats, it must be noted that most rodents are prey rather than predators, and almost never go out into direct sunlight in the middle of the day, since that would make them highly vulnerable to predators. Accordingly, rodents did not evolve with any need for carotenoids to help protect them against UV radiation. Therefore, rodents generally do not metabolize carotenoids in ways comparable to human, and they tend to make relatively poor models for studying the uptake or effects of carotenoids.

However, various manipulations can be used to increase carotenoid uptake in rats and other rodents. As one example, if relatively high concentrations of bile salts or other compounds that help solubilize fatty compounds are added to the diets of mice or rats, the animals will transport higher quantities of carotenoids through the intestinal walls and into circulating blood, which will lead to greater rtes and concentrations of tissue deposition. Therefore, by feeding special diets to mice or rats, various types of research involving zeaxanthin (or other carotenoids) can be carried out in these animals.

It should also be recognized that research which directly uses and includes zeaxanthin will not always be necessary, to do research on mice or rats that can help evaluate and rank candidate nutrients that may be able to work synergistically with zeaxanthin. Instead, the benefits of working with mice or rats usually are limited to initial research, which hopefully will lead to expanded and more expensive research on larger animals and/or humans. Accordingly, mice and rats may be well-suited for evaluating candidate nutrients such as lipoic acid, isoflavonoids, plant polyphenols, omega-3 fatty acids, taurine, carnitine, etc., to evaluate their effects on ocular or vision defects, in tests that will not use or include any zeaxanthin or other carotenoids. Subsequently, after initial evaluations and rankings have been determined by means of initial testing in mice or rats, the most promising candidates can then be tested in more expensive test that will involve zeaxanthin, using animals that metabolize carotenoids in a manner comparable to humans (such as Japanese quails or other suitable birds, or primates), or in human clinical trials.

It should also be recognized that mice, rats, and other rodents do not have pigmented maculas; instead, in general, the only animals that use UV-absorbing carotenoids to protect their retinas are primates, and some species of birds. However, if rats are induced (by bile salts in their diets) to begin taking up substantial quantities of carotenoids into circulating blood, at least some of those carotenoids will be deposited into photoreceptors in the retina, and into the lens of the eye, thereby allowing at least some types of research on those structures.

3. Agents and Methods to Create and Emulate Disorders

Additional options that can be used to evaluate candidate ocular-active nutrients involves the use of certain drugs or diets, to induce certain types of damage that can emulate known ocular disorders. As one example, cataracts can be induced by a drug called buthionin sulfoximine (e.g., Maitra et al 1996), or by feeding lab animals certain types of high-starch diets (e.g., Boreashtein et al 2001). As another example, diabetes can be induced by drugs such as streptozotocin (e.g., Kowluru et al 2003) or allosan.

If the goal of a research project is to study a disorder that involves abnormally high levels of cell growth (such as wet macular degeneration, with excessive blood vessel growth, or certain types of "proliferative retinopathies"), pellets contain cell-stimulating hormones can be implanted into an eye. Such research, using "vascular endothelial growth factor" (VEGF) or "basic fibroblast growth factor" (bFGF), is described in articles such as Yoon et al 2000 and Jousen et al 2000.

Various types of surgical or mechanical interventions can also be used to emulate certain ocular disorders. As one example, clamping off an artery for a fixed period of time is used to create ischemia, then the clamp can be suddenly released, to create a "reperfusion" injury involving oxygen free radicals. In addition, external methods can be used to accelerate certain types of visual impairment. Such methods include, for example, increasing the intensity of ultraviolet and blue light, and increasing the atmospheric oxygen concentrations, in the pens or room where lab animals are being kept.

Any of these methods can impose additional levels of ocular stress an lab animals, thereby substantially accelerating the rates at which they will develop ocular disorders. Accordingly, various candidate ocular-active nutrients can be evaluated for potency and efficacy, by measuring how effectively they can delay, prevent, or reduce the disorders that will rise from the stresses that were imposed on the animals.

4. Japanese Quail and Other Birds

As mentioned above, some types of birds use carotenoid pigments to help protect their retinas against damage by UV light. In most bird species, these pigments are deposited throughout the entire retina, rather than just in a small central area comparable to the maculas of primates. A review of the use of birds, in retinal research, is contained in Fite et al 1991. Japanese quail have become a widely used and accepted bird model for retinal testing, as described in articles such as Fie et al 1993, Fite 1994. Detailed methods for testing this species, to evaluate the ability of zeaxanthin or lutein to protect against retinal damage caused by high-intensity lights, were described in Thomson at al 2002.

In addition, an albino strain of Japanese quail has been developed, which suffers from rapid lens degeneration and cataract formation.

5. Testing of Dogs and Livestock

Among the types of lab animals larger than rodents that are used in vision testing, dogs and livestock tend to be used most commonly, for various reasons.

With respect to dogs, their irises (which are circular) are more similar to human and primate irises, than the vertical-slit irises of cats; in addition, dogs also suffer fairly commonly from cataracts. They can also be induced to incur various types of retinopathies, and there are certain aspects of their vision processing that are of interest to neurology researchers (including limitations in the ability of dogs to generate nerve impulses that will help them recognize and identify things, unless some type of motion is involved that will trigger a set of nerve cell firings). For all of these reasons, dogs are used fairly commonly for ocular and vision research. While they are more expensive than mice or ram, they are less expensive than primate studies or human clinical trials. Accordingly, if dogs are being considered as a potential animal model for studies as disclosed herein, a network of experts who are already familiar with that type of research in dogs can be located, quickly and easily, by a database search for published articles describing vision research in dogs.

Research on eye components or other tissues from various livestock species (including pigs, cows, and sheep) is enabled by an important factor: these animals are killed, in large numbers, at known locations and under controlled conditions (i.e., at slaughterhouses). Therefore, specialized treatment procedures can be carried out on livestock animals shortly before they are killed, and the affected tissues can be harvested at a controlled time, soon thereafter. Alternately, other types of specialized procedures can be carried out on tissue that was harvested immediately after an animal is killed; these types of tissue samples are usually perfused (i.e., placed in specialized equipment that will pump fluids with oxygen and nutrients through or around the tissue), to sustain the tissue in a condition where its cells remain viable and metabolically active for a span of hours or days after the animal was killed. Compared to ocular tissue samples from mice or rats, ocular tissues from animals such as cows or pigs are much easier to handle and work with, and they also provide more relevant results, if dimensional factors are important (such as, for example, when the permeation of a drug or nutrient into or through lens tissue is important).

6. Primate Tests

Primates include lemurs, monkeys, and apes. While they are expensive to raise, keep, and test, they nevertheless provide animal models that, in some situations, will provide better and more applicable and relevant data than any other type of animal test, short of a human clinical trial. Therefore, they must be kept in mind as one option. In many situations, to keep costs under control, it may be possible to "piggyback" a vision-related test on top of some other type of ongoing test (such as a cancer-related test), using the same animals that are being tested for other purposes.

Human Clinical Trials and Meta-Trials

Based on the results of animal tests, as described above and as otherwise known to those skilled in the art, candidate formulation that have performed well n such animal tests can be further evaluated, in clinical trials. As used herein and in common practice, the term "clinical" implies that the subjects will be humans, rather than laboratory animals.

Proper and lawful general procedures for carrying out human clinical trials are described in numerous published articles and books, and are known to thousands of researchers, consultants, and other experts. Those general procedures and requirements will not be discussed or analyzed herein.

However, two aspects of such testing on humans deserve special note and consideration herein.

The first special point worth noting is this: at least some types of ocular or vision-related tests can be designed to speed up the gathering of useful data, when testing patients who are suffering from diseases that gradually manifest or grow worse over a long span of time, such as multiple years. This type of accelerated data gathering can be enabled by various approaches, such as by focusing on selected patients who, at the point in time when they will be tested, are entering or progressing through certain stages that involve accelerated and rapid degeneration and loss of vision acuity.

As one example, among most patients who suffer from the dry form of macular degeneration (which includes roughly 90% of all cases of macular degeneration), their retinas will pass, at some point during the disease, through an intermediate stage called "geographic atrophy". During this stage, distinct patches and areas of degeneration in or around the macula become visible (as indicated by certain types of cellular debris, such as abnormally large pieces of drusen and lipofuscin), in certain types of photographs that can be taken of the retina.

When retinas suffering from dry macular degeneration reach this stage, and begin to suffer from "geographic atrophy" showing clear and distinct patches of degeneration, they have begun (or will soon begin) to suffer from accelerated and rapid retinal degeneration. Briefly, this process can be depicted, in a schematic manner, by using the "S-curve" shown in FIG. 5B. A person suffering from the dry form of macular degeneration typically will spend several years, passing through slow, gradual, and incremental losses of visual acuity, sometimes without even noticing that his or her vision is slowly growing worse (or sometimes choosing to remain silent about it, when they do notice it, for fear of being ordered to stop driving). This long slow stage is represented by the flat slope of the plateau to the left side of the sharper slope.

At some point in time, most victims of macular degeneration will reach a stage when the gradually accumulating stresses seem to begin piling on top of each other, and the person begins to lose visual acuity at an accelerated rate that can no longer be ignored or hidden. When this occurs, if the patent visits an ophthalmologist and has his or her eyes checked, he or she usually will be found to be in the stage called "geographic atrophy." If effective steps are not taken to halt the spread of the damage, it usually will begin accelerating even faster, and will lead to a rapid and severe loss of visual acuity.

When it comes to clinical testing of candidate ocular-active nutrients, patients who are approaching or who have already entered a "rapid acceleration" stage of degeneration can be highly useful and helpful, for carrying out tests that are specially designed to provide relatively rapid data, to help reveal which particular nutrients (out of the various candidates that are being tested) can be the most effective in preventing further degeneration, when combined with zeaxanthin in orally-ingestible formulations and foodstuffs. Accordingly, anyone who is contemplating or designing tests on various candidate ocular-active nutrients, should be alert to the possibility of placing patients who are at the "geographic atrophy" stage of macular degeneration (or at a comparable stage of any other ocular disorder) into a special testing or control population, which can then be analyzed carefully over a shorter period of time than would otherwise be required.

Another important approach that should be carefully considered, by anyone who is contemplating or designing tests on candidate ocular-active nutrients, involves tests that are usually referred to as "meta-trials". In general, these types of tests involve numerous discrete and relatively small data-gathering centers, which are grouped or tied together in ways that allow the data from all of the multiple small centers to be compiled into a larger pool of consistent shared data.

As an example, one of the most promising approaches to human testing of various candidate ocular-active formulations as disclosed herein can use a network of cooperating optometrists and/or ophthalmologists, who are already skilled in examining eyes. Any optometrist or ophthalmologist who wishes to become involved in a meta-trial will need to be instructed (with video, written, or in-person instruction or training, as necessary) in the exact procedures that will need to be followed by all patients enrolled in a test, and by any clerical or healthcare workers who will monitor and review the data gathered a that site.

The procedures that will be used can involve either double-blinded trials, or open-label trials, depending on the desires and goals of the people, companies, or agencies who are organizing and running the study. Monitoring of results can involve any appropriate data-gathering methods, such as visual acuity tests by optometrists (which usually measure "lines of resolution" on standardized eye charts), or more complicated tests by ophthalmologists (such as measurements of pigment densities in lenses or maculas).

Each participating optometrist or ophthalmologist will be responsible for gathering data at his or her site, and one or more workers at the coordinating office will be responsible for (i) creating reporting forms that will help ensure that the data from different sites are uniform and consistent, and (ii) monitoring the quality of the data coming from numerous sites. Participating optometrists or ophthalmologists will be supplied with consistent and exact formulations by a single coordinating office, and if a trial is double-blinded, these products can be in the form of number-coded bottles, containing capsules or tablets that do not indicate whether the contents are test compounds, or controls. Presumably, any such controls likely will contain an anti-oxidant formulation that already has been shown to work at some level of efficacy, such as the AREDS-1 formulation, which contains fairly high dosages of vitamins C and E, beta-carotene, and zinc.

If fifty optometrists or ophthalmologists (each continuing to work out of his or her normal office) are involved, and if each participating optometrist or ophthalmologist enrolls twenty patients in a control group, and twenty patients in a test group, that will generate combined totals of 1000 patients in the control group, and 1000 patients in the test group.

This approach can be used to generate relatively rapid yet statistically powerful data, without placing a age burden on any one particular person or location. Accordingly, meta-trials deserve careful attention, since they offer highly promising and relatively rapid yet relatively inexpensive methods for carrying out human clinical trials, involving large numbers of test and control subjects, on candidate ocular-active combinations as described herein.

Candidate Ocular Active Nutrients

As mentioned in the Summary of the Invention, eight categories of ocular-active nutrients are identified herein, which are believed to offer good and promising candidates for early evaluation, to determine whether they can provide synergistic benefits when orally ingested along with zeaxanthin. These eight categories are summarized and described below.

Most of the compounds mentioned below have one or more "chiral" carbon atoms, and therefore have different stereoisomers. As a general rule, if any one particular stereoisomer is predominant, in plant sources or in animals, then a strong presumption arises that steps should be taken to provide the natural stereoisomer in a purified or semi-purified form, in any ocular-active nutrient that is being sold or administered to people who wish to protect their eye health. Various known factors suggest that the eye is one of the most "stereo-specific" organs anywhere in the body, and is highly sensitive to differences in stereoisomers. In many cases, this goal can be accomplished by using plant extracts, or by using compounds that have been synthesized by chemically modifying plant-derived stereospecific precursors.

1. Lipoic Acid

This is a fatty acid having 8 carbon atoms in a straight chain, with the carboxy group at the 18 carbon atom, and with the #1 and #3 carbon atoms both coupled to mercaptan groups (—SH, also called sulfhydryl or sulfide groups). In the reduced form, the two mercaptan groups stay separated from each other, with hydrogen protons attached to the sulfur atoms in both pendant groups. In the oxidized form, the hydrogen protons are removed, and the two sulfur atoms bond to each other, to form a five-member ring with the #1, #2, and #3 carbon atoms forming the remainder of the ring.

Because it can convert beck and forth between a reduced form and an oxidized form, lipoic acid can help reduce and prevent unwanted oxidation of cells and tissues, and under some circumstance, it can also help regenerate vitamin E (Stoyanovsky et al 1995). Other articles that describe lipoic acid's ability to protect ocular tissues in various tests include Packer 1994, Obrosova et al 1998, Borenshtein et al 2001, Chidlow 2002, and Goralska et al 2003.

Maitra et al 1996 reported that the naturally-occurring "R" (dextrorotatory) stereoisomer has better anti-oxidant activity than the S (levorotatory) isomers that are found in synthetic racemic mixtures. Accordingly, lipoic acid preparations having pure or enriched R stereoisomers are preferred for testing and evaluation as disclosed herein.

2. Omega-3 Fatty Acids

Certain types of compounds that animals must eat in their diets are called "essential fatty acids", because (i) animals need them, mainly for cell membrane formation, but animals cannot synthesize them; (ii) they contain a chain of carbon atoms with a length (usually ranging from about 10 to about 24 carbon atoms) that will form a fatty substance that is solid or semi-solid at room temperature; and (ii) the last carbon atom in the carbon chain is part of a carboxylic acid group (—COOH).

In humans, the three most important essential fatty acids are docosa-hexaenoic acid (abbreviated as DHA), eicosapentaenoic acid (EPA), and alpha-linolenic acid (ALA). All three of these compound are called omega-3 fatty acids, since the #3 carbon atom (counting from the non-acid end of the chain) is the first carbon atom that is involved in an unsaturated bond. All three of those omega-3 fatty acids are present in relatively high concentrations in certain types of fish oils, and they can also be obtained from other natural sources, such as certain types of marine algae. They are associated with a number of health benefits, including cardiovascular benefits, anti-cancer activity, etc., so they are of substantial interest throughout the entire field of dietary supplements, as described in articles such as Connor 2000.

Omega-6 fatty acids (with the first double-bond positioned between the #6 and #7 carbon atoms in the carbon chain) are more abundant in nature; however, their health benefits are not as great as for omega-3 fatty acids, and most people already get too many omega-6 fatty acids and not enough omega-3 fatty acids in their diets. Therefore, if a dietary supplement contains a mixture of omega-3 and omega-6 fatty acids, it preferably should contain at least about 30%, and preferably 50% or more, of the omega-3 compounds.

Among the omega-3 fatty acids, DHA has a more important role in mammalian metabolism than EPA, and ALA is generally regarded as merely a precursor to DHA and EPA. Therefore, in purified or semi-purified preparations, DHA is generally the preferred compound, and it has received the most study. Its activities and effects in eyes are described in articles such as Jeffrey et al 2001, Poli et at 2001, Murayama et al 2002, and Rotsiein et al 2003.

3. Plant-Derived Active Agents (Flavonoids, Anthocyanins, Plant Polyphenolics, and Phytonutrients)

A third category of candidate ocular-active nutrients that is of interest herein includes a umber of plant-derived compounds, which can be referred to by terms that include flavonoids (or bioflavonoids), anthocyanin, plant polyphenolics, or phytonutrients. These labels overlap heavily with each other, and compounds that fall within labels are described in various articles such as Beecher 1999 and Beecher 2003. The molecular structures for each of the named compounds listed below are publicly known, and can be located in various public sources (e.g., the chemical structures of numerous flavonoids, both common and rare, are nicely illustrated and organized at http://www.friedli.com/herbs/phytochem/flavonoids.html).

Compounds that fall within the categories of flavonoids, anthocyanins, plant polyphenolics, or phytonutrients can include either or both of the following: (i) non-purified or semi-purified multi-component mixtures that have been extracted from the fruits, leaves, seeds, nuts, or other parts of various known plants, such as bilberry, grapeseed, green tea, or soybeans; or, (ii) specific known and purified compounds (or limited mixtures of a small number of similar and related compounds) from such plants, such as quercetin, genestein, diazedem, fisetin, luteolin, resveretrol, and pycogenol.

These and various other similar known agents have different specific activities and roles, and each one needs to be considered separately. For example, most flavonoid compounds reduce the activity of an enzyme called aldose reductase. This enzyme converts certain types of beneficial sugars (such as glucose) into sugar-alcohols (such as sorbitol) that will cause problems if they accumulate in excessive quantities. Sorbitol is an important causative factor in cataract formation, especially among diabetics. Therefore, flavonoids that inhibit aldose reductase enzymes can help prevent or slow down cataract formation (e.g., Jung et at 202, Matsuda et at 2002).

The specific activities, in animal eyes, of any known plant polyphenol (or flavonoid, anthocyanin, phytonutrient, etc.)

that has been studied in animals can be identified fairly easily, by searching the free database that is maintained by the National Library of Medicine. As examples, resveretrol reportedly can suppress vascularization (e.g., Brakenhielm et al 2001), and is a good antioxidant and free radical scavenger (Lorenz et al 2003), while genistein reportedly inhibits certain protein kinase enzymes, and can help suppress unwanted types of cell-signaling pathways (e.g., Yoon 2000).

4. Taurine

Taurine is the common name for 2-amino-ethane sulfonic acid, a "conditionally essential nutrient" that is present in milk and elsewhere. Taurine's ability to protect various ocular tissues in various types of tests (especially involving diabetic pathologies) is described in articles such a Devamanoharan et al 1998, Obrosova et al 1999 and 2001, Chen et al 2000, Militante et al 2002, Pasantes-Morale et al 2002, and DiLeo et al 2003.

5. Carnitine

L-Carnitine is a sulfur-containing amino acid (not one of the 20 primary amino acids used in protein synthesis) that is formed in the liver and certain other tissues. It is believed to facilitate the transport of fatty acids into mitochondria, for certain types of oxidation. Certain esters of carnitine (mainly acetyl-L-carnitine) are preferred for oral ingestion.

Carnitine's ability to help prevent or treat ocular disorders is described in articles such a Pessotto et al 1997, Peluso et al 2001, Alagoz et al 2002, and Feher et al 2003. The acetyl-L-carnitine precursor is one of three ingredients (along with omega-3 fatty acids, and coenzyme Q10) in an ocular formulation called PHOTOTROP™, sold by the Sigma Tau Company.

6. Coenzyme-Q10

An enzyme cofactor known as Coenzyme-Q10 (the Q stands for quinone) is a known anti-oxidant that provides energy-related support to mitochondria. Mitochondria are organelles, inside animal cells, that are enclosed within their own membranes and that have their own set of genes (these genes even use their own special genetic code, which is slightly different from the standard genetic code used in the nucleus of a cell). In a truly remarkable feat of adaptive biology, mitochondria actually are the descendants of tiny anaerobic bacteria, which invaded larger cells billions of years ago, and which then established a symbiotic relationship with their host cells. In this symbiotic relationship, the invaders-turned-guests carry out processes known as "oxidative phosphorylation", which is a crucial part of energy metabolism in the host cells. Because of this role, mitochondria are sometimes referred to as the "furnaces" that handle the burning operations that supply heat and power to the rest of the cell.

When mitochondria are under severe stress, they begin releasing certain types of cytochrome compounds, which will then begin acting as signalling compounds, which will activate a process called "apoptosis", also referred to as "programmed cell death". Apoptosis is a natural process that is beneficial in most situations, since it gives tissues and organs a way to clean up and get rid of dead and dying cells, and replace them with newly-formed and healthy cells. However, in some situations (especially involving neurons, which are extremely difficult and often impossible to replace), apoptosis can lead to severe problems, including (in eye tissues) the unprogrammed and unwanted death and destruction of neurons in the retina. Therefore, by helping stabilize mitochondria, Coenzyme-Q10 can help prevent the release of mitochondrial cytochromes that would lead to unwanted cell deaths, in ocular tissues that are struggling to cope with a serious disorder.

As mentioned above, Coenzyme Q10 is one of the three ingredients in an ocular formulation called PHOTOTROP™, sold by the Sigma Tau Company.

7. Carnosine

Carnosine is a di-peptide, formed when alanine and histidine bond to each other. It can bond to and quench aldehydes, which are potentially dangerous reactive molecules that can otherwise cause random and unwanted modifications (such as glycosylation or crosslinking) to proteins. The most commonly used orally-ingestible form of carnosine is an ester precursor, N-alpha-acetyl-carnosince. Eyedrops containing carnosine also have been developed and are being publicly sold in Europe.

The protective activities and effects of carnosine in ocular tissues are described in articles such as Maichuk et al 1997, Hipkiss et al 1998, and Babizhayev et al 2002.

8. Glutathione Boosters

Glutathione is a tri-peptide molecule, formed by three amino acids linked together, with cysteine in the middle. Cysteine has a highly reactive sulfur group (—SH) as its side chain. This allows the glutathione tri-peptide to become bonded to other compounds.

With the help of enzymes such as glutathione-S-transferse, glutathione most commonly gets bonded to waste metabolites. This makes the waste products more soluble in water, which in turn helps cells and tissues eliminate those wastes, through pathways that typically end up in urine.

Since the glutathione system provides a useful pathway that helps cells and tissues get rid of waste products, nutrients that can stimulate the production or metabolism of glutathione can help badly-stressed cells and tissues cope more successfully with their waste-handling problems. One such nutrient is N-acetyl cysteine, an ester that when ingested orally will release cysteine, the sulfur-containing amino acid that sits at the center of the glutathione tripeptide. Other candidates agents that are believed to boost glutathione production or metabolism include selenium, pyridoxine, and riboflavin. These are disclosed, as agents that can help treat macular degeneration, in U.S. Pat. No. 5,075,116 (LaHaye 1991).

The Areds-1 Components

In addition to the eight categories of ocular-active nutrients listed above (none of which were tested during the AREDS-1 trial in the 1990's), three additional types of compounds that were tested in the AREDS-1 trial also deserve attention. These compounds are also discussed in U.S. Pat. No. 6,660,297 (Bartels et al 2003).

Tocopherol compounds, such as alpha-tocopherol (vitamin E), merit special attention, because of an important physiological factor. Carotenoids tend to be most effective, as antioxidants, in the presence of relatively low oxygen concentrations. By contrast, tocopherols tend to become more and more effective, as antioxidants, when oxygen concentrations grow higher. Therefore, a combination of zeaxanthin with one or more tocopherols is likely to provide a good "broad-spectrum" antioxidant, where each compound can work most effectively under the conditions where the other compound is weakest.

Vitamin C has its own well-known benefits, and it is one of the few vitamins or anti-oxidants that is water-soluble. Therefore, if a water-soluble anti-oxidant such as Vitamin C is coadministered with zeaxanthin (a hydrophobic, oil-soluble anti-oxidant), the two of them together are likely to be more effective than either one can be by itself.

Zinc also has a crucially important and valuable role in biology, because it is the only essential mineral (or transition metal) that has no reduction-oxidation potential. Its electric charge is completely neutral; it will not seek to take protons or electrons away from proteins or DNA, and it will not seek to get rid of protons or electrons by pushing them off onto proteins or DNA. In addition, it can bond in a stable manner to one, two, three, or even four other molecules. Therefore, it evolved into an essential cofactor in hundreds of enzymes and thousands of DNA-regulatory proteins, and it is very widely used by proteins to stabilize a variety of three-dimensional conformations, ranging from the protruding "finger domains" in zinc-finger proteins, to the "deep cleft" domains in carbonic anhydrase enzymes. It also helps stabilize cell membranes, promotes wound-healing, and even has significant microbicidal and bacteriostatic activity.

Because it is a known beneficial, stabilizing, membrane-protecting agent, oral dosages of zinc were tested, years ago, to determine whether they could help people suffering from macular degeneration and other ocular problems. The results were good, although not especially strong, as described in articles such as Newsome et al 1988, Yuzbasiyan et al 1989, Hawkins 1991, Trempe 1992, and Beaumont 1993. Therefore, it was included in the AREDS-1 trial, and the benefits it provided were: (i) strong enough to roughly match the benefits provided by a combination of vitamins A, C, and E, and (ii) strong enough to push the benefits offered by vitamins A, C, and E into a higher category of significance.

Accordingly, zinc is regarded as one of the more promising candidate agents, for testing as described herein. However, it is suspected that the benefits of zinc, for at least mast patients, likely can be completely achieved by dosages in the range of about 40 mg/day (which is only about half of the dosages used in the AREDS-1 trial), or possibly even less. Accordingly, if substantial synergistic benefits can be provided by 40 mg/day or lower dosages of zinc, when combined with zeaxanthin, those lower dosages of zinc can help avoid various concerns over zinc-induced anemia, and/or the need for yet another additive (such as copper sulfate), that were raised by the 80 mg dosages used in the AREDS-1 trial.

Thus, there has been shown and described a new and useful means for identifying agents that can perform synergistically with zeaxanthin, in pharmaceutical, dietary, or food preparations that can help protect eye health and treat ocular disorders. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Alagoz G, et al, "L-carnitine in experimental retinal ischemia-reperfusion injury," Ophthalmologica. 2002 March-April; 216(2): 144-50

Areiss F M, et al, "Antioxidant effect of flavonoids after ascorbate/Fe(2+)-induced oxidative stress in cultured retinal cells," Biochem Pharmacol. 2001 Jul. 1; 62(1): 111-8

Babizhayev M A, et al, "Efficacy of N-acetylcarnosine in the treatment of cataracts," Drugs R D. 2002; 3(2): 87-103

Beaumont P., "Zinc and macular degeneration," Arch Ophthalmol. 111: 1023 (1993)

Beecher G R, "Overview of dietary flavonoids: nomenclature, occurrence and intake," J Nutr. 2003 October; 133(10): 3248S-3254S Beecher G R, "Phytonutrients' role in metabolism: effects on resistance to degenerative processes," Nutr Rev. 1999 September; 57(9 Pt 2): S3-6

Borenshtein D, et al, "Cataract development in diabetic sand rats treated with alpha-lipoic acid and its gamma-linolenic acid conjugate," Diabetes Metab Res Rev. 2001 January-February; 17(1): 44-50

Brakenhielm E, et al, "Suppression of angiogenesis, tumor growth, and wound healing by resveratrol, a natural compound in red wine and grapes," FASEB J. 2001 August; 15(10): 1798-800

Cao Y, et al, "Antiangiogenic mechanisms of diet-derived polyphenols," J Nutr Biochem. 2002 July; 13(7): 380-390

Castillo M, et al, "Effects of hypoxia on retinal pigmented epithelium cells: protection by antioxidants," Ophthalmic Res. 2002 November-December; 34(6): 338-42

Chen F, et al, "An experimental research of taurine on H2O2-induced bovine lens epithelial cell apoptosis," Zhonghua Yan Ke Za Zhi. 2000 July; 36(4): 272-4, 17

Chidlow G, at al, "Alpha-lipoic acid protects the retina against ischemia-reperfusion," Neuropharmacology. 2002 November; 43(6): 1015-25

Connor W E., "Importance of omega-3 fatty acids in health and disease," Am J Clin Nutr. 2000 January; 71(1 Suppl): 171S-5S.

Devamanoharan P S, at al, "Oxidative stress to rat lens in vitro: protection by taurine," Free Radic Res. 1998 September; 29(3): 189-95

DiLeo M A, et al, "Potential therapeutic effect of antioxidants in experimental diabetic retina: a comparison between chronic taurine and vitamin E plus selenium supplementations," Free Radic Res. 2003 March; 37(3): 323-30

Erhud I, at al, "Consumption of black currants, lingonberries and bilberries increases serum quercetin concentrations," Eur J Clin Nutr. 2003 January; 57(1): 37-42

Feher J, et al, "Mitotropic compounds for the treatment of age-related macular degeneration. The metabolic approach and a pilot study," Ophthalmologica. 2003 September-October; 217(5): 351-7

Goralska M, et al, "Alpha lipoic acid changes iron uptake and storage in lens epithelial cells," Exp Eye Res. 2003 February; 76(2): 241-8

Hawkins W R., "Zinc supplementation for macular degeneration," Arch Ophthalmol. 109: 1345 (1991)

Hipkiss A R, et al, "Pluripotent protective effects of carnosine, a naturally occurring dipeptide," Ann N Y Acad Sci. 1998 Nov. 20; 854: 37-53

Jeffrey B G, at al, "The role of docosahexanoic acid in retinal function," Lipids. 2001 September; 36(9): 859-71

Joassen A M, et al, "Treatment of corneal neovascularization with dietary isoflavonoids and flavonoids," Exp Eye Res. 2000 November; 71(5): 483-7

Jung S H, et al, "Isoflavonoids from the rhizomes of Belamcanda chinensis and their effects on aldose reductase and sorbitol accumulation in streptozotocin induced diabetic rat tissues," Arch Pharm Res. 2002 June; 25(3): 306-12

Kahkonen M P, at al, "Berry phenolics and their antioxidant activity," J Agric Food Chem. 2001 August; 49(8): 4076-82

Kilic F, et al, "Modelling cortical cataractogenesis XX. In vitro effect of alpha-lipoic acid on glutathione concentrations in lens in model diabetic cataractogenesis," Biochem Mol Biol Int. 1998 October; 46(3): 585-95

Kocer I, et al, "Protection of the retina from ischemia-reperfusion injury by L-carnitine in guinea pigs," Eur J Ophthalmol. 2003 January-February; 13(1): 80-5

Kowluru R A., "Diabetes-induced elevations in retinal oxidative stress, protein kinase C and nitric oxide are interrelated," Acts Diabetol. 2001 December; 38(4): 179-85

Kowluru R A, et al, "Diabetes-induced mitochondrial dysfunction in the retina," Invest Ophthalmol Vis Sci. 2003 December; 44(12): 5327-34

Lorenz P, et al, "Oxyresveratrol and resveratrol are potent antioxidants and free radical scavengers: effect on nitrosative and oxidative stress derived from microglial cells," Nitric Oxide. 2003 September; 9(2): 64-76

Maichuk I F, et al, "[Development of carnosine eyedrops and assessing their efficacy in corneal diseases] Vestn Oftalmol. 1997 November-December; 113(6): 27-31

Maitra I. et al, "Stereospecific effects of R-lipoic acid on buthionine sulfoximine-induced cataract formation in newborn rats," Biochem Biophys Res Commun. 1996 Apr. 16; 221(2): 422-9

Manzanas L, et al, "Oral flavonoids, chromocarb diethylamine salt and cyaninosides chloride, to eliminate lipoperoxidation postvitrectomy," Exp Eye Res. 2002 January; 74(1): 23-8

Matsuda H, et al, "Structural requirements of flavonoids and related compounds for aldose reductase inhibitory activity," Chem Pharm Bull (Tokyo). 2002 June; 50(6): 788-95

Militante J D, et al, "Taurine: evidence of physiological function in the retina," Nutr Neurosci. 2002 April; 5(2): 75-90

Murayama K, et al, "Fish oil (polyunsaturated fatty acid) prevents ischemic-induced injury in the mammalian retina," Exp Eye Res. 2002 June; 74(6): 671-6

Newsome, D. A., et al, "Oral zinc in macular degeneration," Arch. Ophthalmol. 106: 192-198 (1988)

Obrosova I G, et al, "Taurine counteracts oxidative stress and nerve growth factor deficit in early experimental diabetic neuropathy," Exp Neurol. 2001 November; 172(1): 211-9

Obrosova I, et al, "Diabetes-induced changes in lens antioxidant status, glucose utilization and energy metabolism: effect of DL-alpha-lipoic acid," Diabetologia. 1998 December; 41(12): 1442-50

Obrosova I G, et al, "Early changes in lipid peroxidation and antioxidative defense in diabetic rat retina: effect of DL-alpha-lipoic acid," Eur J Pharmacol. 2000 Jun. 9; 398 (1): 139-46

Obrosova I G, et al, "Effect of dietary taurine supplementation on GSH and NAD(P)-redox status, lipid peroxidation, and energy metabolism in diabetic precataractous lens," Invest Ophthalmol Vis Sci. 1999 March; 40(3): 680-8

Okuyama H, et al, "alpha-linolenate-deficiency-induced alterations in brightness discrimination learning behavior and retinal function in rats," World Rev Nutr Diet. 2001; 88: 35-40

Packer L., "Antioxidant properties of lipoic acid and its therapeutic effect in prevention of diabetes complications and cataracts," Ann N Y Acad Sci. 1994 Nov. 17; 738: 257-64

Pasantes-Morales H, et al, "Treatment with taurine, diltiazem, and vitamin E retards the progressive visual field reduction in retinitis pigmentosa: a 3-year follow-up study," Metab Brain Dis. 2002 September; 17(3): 183-97.

Peluso G, et al, "Carnitine protects the molecular chaperone activity of lens alpha-crystallin and decreases the post-translational protein modifications induced by oxidative stress," FASEB J. 2001 July; 15(9): 1604-6

Pessotto P, et al, "In experimental diabetes the decrease in the eye of lens carnitine levels is an early important and selective event," Exp Eye Res. 1997 February; 64(2): 195-201

Polit L, et al, "Effects of docosahexaenoic acid on retinal development: cellular and molecular aspects," Lipids. 2001 September; 36(9): 927-35

Robert A M, et al, "[Protection of cornea against proteolytic damage. Experimental study of procyanidolic oligomers (PCO) on bovine cornea] J Fr Ophtalmol. 2002 April; 25(4): 351-5

Rotstein N P, et al, "Protective effect of docosahexaenoic acid on oxidative stress-induced apoptosis of retina photoreceptors," Invest Ophthalmol Vis Sci. 2003 May; 44(5): 2252-9

Sparrow J R, et al, "A2E-epoxides damage DNA in retinal pigment epithelial cells. Vitamin E and other antioxidants inhibit A2E-epoxide formation," J Biol Chem. 2003 May 16; 278(20): 18207-13. Epub 2003 Mar. 19

Stoyanovsky D A, et al, "Endogenous ascorbate regenerates vitamin E in the retina directly and in combination with exogenous dihydrolipoic acid," Curr Eye Res. 1995 March; 14(3): 181-9

Thomson L R, et al, "Elevated retinal zeaxanthin and prevention of light-induced photoreceptor cell death in quail," Invest Ophtalmol Vis Sci. 2002 November; 43(11): 3538-49.

Trempe C. L., "Zinc and macular degeneration," Arch Ophthalmol. 110: 1517 (1992)

Yamakoshi J, et al, "Procyanidin-rich extract from grape seeds prevents cataract formation in hereditary cataractous (ICR/f) rats," J Agric Food Chem. 2002 Aug. 14; 50(17): 4983-8

Yoon H S, et al, "Genistein produces reduction in growth and induces apoptosis of rat RPE-J cells," Curr Eye Res. 2000 March; 20(3): 215-24

Yuzbasiyan, G. V., et al, "The therapeutic use of zinc in macular degeneration," Arch Ophthalmol. 107: 1723-24 (1989)

The invention claimed is:

1. A nutrient formulation in an oral ingestion form for a daily dosage, comprising:
   a. at least 3 milligrams of zeaxanthin that is present in 3R-3'R stereoisomer form and is substantially free of meso-zeaxanthin stereoisomers;
   b. zinc at a dosage that does not exceed 40 milligrams of elemental zinc;
   c. vitamin C that is presented in the form of ascorbic acid;
   d. at least one tocopherol that provides anti-oxidant activity;
   e. omega-3 fatty acids including docosa-hexaenoic acid (DHA) and eicosa-pentaenoic acid (EPA);
   f. lipoic acid; and
   wherein the nutrient formulation is provided in the form selected from the group consisting of capsules, tablets, liquids, and powders for oral ingestion.

2. The nutrient formulation of claim 1, wherein the omega-3 fatty acids are derived from fish oil.

3. The nutrient formulation of claim 1, wherein the nutrient formulation is present in a form that provides sustained release over a span of at least 3 hours following ingestion.

4. The nutrient formulation of claim 1, wherein a plurality of capsules is required to achieve the at least 3 milligram daily dosage of zeaxanthin.

5. The nutrient formulation of claim 1, wherein the daily dosage of zeaxanthin is at least 10 milligrams.

6. A nutrient formulation in an oral ingestion form for a daily dosage, comprising:
   a. at least 3 milligrams of zeaxanthin that is present in 3R-3'R stereoisomer form and is substantially free of meso-zeaxanthin stereoisomers;
   b. zinc at a dosage that does not exceed 40 milligrams of elemental zinc;
   c. vitamin C that is presented in the form of ascorbic acid;
   d. at least one tocopherol that provides anti-oxidant activity, the at least one tocopheral including vitamin E; and
   wherein the nutrient formulation is presented in the form of pills or capsules that contain oily carrier materials to increase the uptake of the nutrient formulation.

7. The nutrient formulation of claim 6, further comprising omega-3 fatty acids.

8. The nutrient formulation of claim 7, wherein the omega-3 fatty acids are derived from fish oil.

9. The nutrient formulation of claim 6, wherein said nutrient formulation is present in a form that provides sustained release over a span of at least 3 hours following ingestion.

10. The nutrient formulation of claim 6, wherein the daily dosage of zeaxanthin is at least 10 milligrams.

11. The nutrient formulation of claim 6, wherein the formulation further includes lipoic acid.

12. The nutrient formulation of claim 6, wherein the formulation is in the form of capsules containing oily carrier materials.

13. The nutrient formulation of claim 1, wherein the formulation is in the form of capsules containing oily carrier materials.

14. The nutrient formulation of claim 1, wherein the at least one tocopherol includes vitamin E.

* * * * *